US 8,431,589 B2

(12) United States Patent
Baenteli et al.

(10) Patent No.: US 8,431,589 B2
(45) Date of Patent: *Apr. 30, 2013

(54) 2,4-DIAMINOPYRIMIDINE DERIVATIVES

(75) Inventors: Rolf Baenteli, Basel (CH); Gerhard Zenke, Rheinfelden (DE); Nigel Graham Cooke, Oberwil (CH); Rudolf Duthaler, Bettingen (CH); Gebhard Thoma, Lörrach (DE); Anette Von Matt, Biel-Benken (CH); Toshiyuki Honda, Tsukuba (JP); Naoko Matsuura, Tsukuba (JP); Kazuhiko Nonomura, Tsukuba (JP); Osamu Ohmori, Tsukuba (JP); Ichiro Umemura, Tsukuba (JP); Klaus Hinterding, Wittlingen (DE); Christos Papageorgiou, Riedisheim (FR)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/069,816

(22) Filed: Mar. 23, 2011

(65) Prior Publication Data

US 2011/0172231 A1 Jul. 14, 2011

Related U.S. Application Data

(62) Division of application No. 10/507,060, filed as application No. PCT/EP03/02710 on Mar. 14, 2003, now Pat. No. 7,943,627.

(30) Foreign Application Priority Data

Mar. 15, 2002 (GB) .................................. 0206215.6

(51) Int. Cl.
C07D 239/48 (2006.01)
A61K 31/505 (2006.01)

(52) U.S. Cl.
USPC .......................................... 514/275; 544/323

(58) Field of Classification Search .................. 544/323; 514/275
See application file for complete search history.

(56) References Cited

U.S. PATENT DOCUMENTS

| | | | |
|---|---|---|---|
| 3,361,749 A | 1/1968 | Matter et al. | |
| 3,432,493 A | 3/1969 | Short | |
| 5,958,935 A | 9/1999 | Davis et al. | |
| 6,048,866 A | 4/2000 | Hutchings et al. | |
| 6,093,716 A | 7/2000 | Davis et al. | |
| 6,114,333 A | 9/2000 | Davis et al. | |
| 6,235,746 B1 | 5/2001 | Davis et al. | |
| 6,337,335 B1 | 1/2002 | Hutchings et al. | |
| 6,593,326 B1 | 7/2003 | Bradbury et al. | |
| 7,514,446 B2 | 4/2009 | Davis-Ward et al. | |
| 7,671,063 B2 | 3/2010 | Baenteli et al. | |
| 2006/0100227 A1 | 5/2006 | Baenteli et al. | |
| 2006/0247241 A1 | 11/2006 | Garcia-Echeverria et al. | |
| 2007/0010668 A1 | 1/2007 | Davis-Ward et al. | |
| 2008/0132504 A1 | 6/2008 | Garcia-Echeverria et al. | |

FOREIGN PATENT DOCUMENTS

| | | |
|---|---|---|
| EP | 0 945 443 A1 | 9/1999 |
| EP | 1 054 004 A1 | 11/2000 |
| EP | 1 184 376 A1 | 3/2002 |
| WO | WO 95/15952 A1 | 6/1995 |
| WO | WO 96/28427 A1 | 9/1996 |
| WO | WO 97/19065 | 5/1997 |
| WO | WO 98/11094 A1 | 3/1998 |
| WO | WO 98/15547 A1 | 4/1998 |
| WO | WO 98/41512 A1 | 9/1998 |
| WO | WO 99/50250 A1 | 10/1999 |
| WO | WO 00/12485 A1 | 3/2000 |
| WO | WO 00/27825 A1 | 5/2000 |
| WO | WO 00/31068 A1 | 6/2000 |
| WO | WO 00/33844 A1 | 6/2000 |
| WO | WO 00/39101 A1 | 7/2000 |
| WO | WO 00/78731 A1 | 12/2000 |
| WO | WO 01/25220 A1 | 4/2001 |
| WO | WO 01/27089 A1 | 4/2001 |
| WO | WO 01/29009 A1 | 4/2001 |
| WO | WO 01/32632 A2 | 5/2001 |
| WO | WO 01/47897 A1 | 7/2001 |
| WO | WO 01/60816 A1 | 8/2001 |
| WO | WO 01/62233 A2 | 8/2001 |

(Continued)

OTHER PUBLICATIONS

Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*

(Continued)

Primary Examiner — Deepak Rao
(74) Attorney, Agent, or Firm — Paul D. Strain, Esq.; Strain & Strain PLLC

(57) ABSTRACT

There are provided compounds of formula I (I)

wherein X, $R^1$, $R^2$, $R^3$, $R^4$, $R^5$, $R^6$, $R^7$, $R^8$ and $R^9$ are as indicated in claim 1, useful in disorders where ZAP-70 and/or Syk inhibition plays a role or caused by a malfunction of signal cascades connected with FAK.

10 Claims, No Drawings

FOREIGN PATENT DOCUMENTS

| | | |
|---|---|---|
| WO | WO 01/64654 A1 | 9/2001 |
| WO | WO 01/64655 A1 | 9/2001 |
| WO | WO 01/64656 A1 | 9/2001 |
| WO | WO 02/056888 A2 | 7/2002 |
| WO | WO 03/018021 A1 | 3/2003 |
| WO | WO 03/030909 A1 | 4/2003 |
| WO | WO 03/063794 A2 | 8/2003 |
| WO | WO 03/066601 A1 | 8/2003 |
| WO | WO 03/078404 A1 | 9/2003 |
| WO | WO 03/095448 A1 | 11/2003 |
| WO | WO 2004/002964 A1 | 1/2004 |
| WO | WO 2004/056786 A2 | 7/2004 |
| WO | WO 2004/074244 A2 | 9/2004 |
| WO | WO 2004/080980 A1 | 9/2004 |
| WO | WO 2005/016894 A1 | 2/2005 |
| WO | WO 2005/026130 A1 | 3/2005 |
| WO | WO 2006/068770 A1 | 6/2006 |

OTHER PUBLICATIONS

European Search Report, Application No. 10163904.5, Mar. 3, 2011, 7 pgs.
Rolf Baenteli, U.S. PTO Supplemental Notice of Allowance, U.S. Appl. No. 10/507,060, Mar. 31, 2011, 5 pgs.
Basford et al., CAPLUS Abstract 41:763 (1947), pp. 7810-7812.
Carlos Garcia-Echeverria, U.S. PTO Notice of Allowance, U.S. Appl. No. 10/549,250, Feb. 7, 2011, 7 pgs.
Carlos Garcia-Echeverria, U.S. PTO Office Action, U.S. Appl. No. 10/549,250, Jan. 21, 2011, 5 pgs.
Carlos Garcia-Echeverria, U.S. PTO Office Action, U.S. Appl. No. 10/549,250, Jan. 28, 2009, 24 pgs.
Carlos Garcia-Echeverria, U.S. PTO Office Action, U.S. Appl. No. 10/549,250, May 20, 2010, 11 pgs.
Carlos Garcia-Echeverria, U.S. PTO Office Action, U.S. Appl. No. 10/549,250, Oct. 12, 2010, 10 pgs.
Carlos Garcia-Echeverria, U.S. PTO Office Action, U.S. Appl. No. 10/549,250, Nov. 12, 2009, 15 pgs.
Carlos Garcia-Echeverria, U.S. PTO Office Action, U.S. Appl. No. 10/568,367, Jan. 30, 2009, 28 pgs.
Carlos Garcia-Echeverria, U.S. PTO Office Action, U.S. Appl. No. 10/568,367, Mar. 16, 2010, 7 pgs.
Carlos Garcia-Echeverria, U.S. PTO Office Action, U.S. Appl. No. 10/568,367, Oct. 27, 2009, 11 pgs.
Carlos Garcia-Echeverria, U.S.PTO Notice of Allowance, U.S. Appl. No. 10/568,367, Oct. 4, 2010, 12 pgs.
Coopman et al., "The Syk tyrosine kinase suppresses malignant growth of human breast cancer cells", Nature, vol. 406 (2000), pp. 742-747.
Dirks et al., "Expression and Functional Analysis of the Anaplastic Lymphoma Kinase (ALK) Gene in Tumor Cell Lines", Int. J. Cancer, vol. 100 (2002), pp. 49-56.
Dolly Ghosh, "2,4-Bis(Arylamino)-6-Methyl Pyrimidines as Antimicrobial Agents", J. Indian Chem. Soc., vol. 58, No. 5 (1981), pp. 512-513.
Ghoneim et al., "Synthesis and Evaluation of some 2-, 4- and 2,4-Di-substituted-6-methylpyrimidine Derivatives for Antimicrobial Activity", J. Indian Chem. Soc., vol. 63, No. 10 (1986), pp. 914-917.
Ghosh, "2,4-Bis(arylamino)pyrimidines as antimicrobial agents", J. Med. Chem., vol. 9, No. 3 (1966), pp. 423-424.
Gosh et al., "2,4-Bis(arylamino)-5-methylpyrimidines as Antimicrobial Agents", Journal of Medicinal Chemistry, vol. 10, No. 5 (1967), pp. 974-975.
Rolf Baenteli, U.S. PTO Notice of Allowance, U.S. Appl. No. 10/507,060, Mar. 16, 2010, 8 pgs.
Rolf Baenteli, U.S. PTO Notice of Allowance, U.S. Appl. No. 10/507,060, Aug. 12, 2010, 10 pgs.
Rolf Baenteli, U.S. PTO Notice of Allowance, U.S. Appl. No. 10/507,060, Sep. 2, 2010, 8 pgs.
Rolf Baenteli, U.S. PTO Notice of Allowance, U.S. Appl. No. 10/507,060, Dec. 27, 2010, 9 pgs.
Rolf Baenteli, U.S. PTO Notice of Allowance, U.S. Appl. No. 11/377,716, Oct. 13, 2009, 7 pgs.
Rolf Baenteli, U.S. PTO Office Action, U.S. Appl. No. 10/507,060, Apr. 7, 2008, 21 pgs.
Rolf Baenteli, U.S. PTO Office Action, U.S. Appl. No. 10/507,060, May 5, 2009, 11 pgs.
Rolf Baenteli, U.S. PTO Office Action, U.S. Appl. No. 10/507,060, Dec. 7, 2009, 6 pgs.
Rolf Baenteli, U.S. PTO Office Action, U.S. Appl. No. 10/507,060, Dec. 16, 2008, 9 pgs.
Rolf Baenteli, U.S. PTO Office Action, U.S. Appl. No. 11/377,716, Jun. 1, 2009, 16 pgs.
Rolf Baenteli, U.S. PTO Office Action, U.S. Appl. No. 11/377,716, Dec. 12, 2008, 21 pgs.
Simone, Oncology: Introduction, Cecil Textbook of Medicine, 20th Edition, vol. 1 (1996), pp. 1004-1010.
Traxler, "Protein Tyrosine Kinase Inhibitors in Cancer Treatment", Expert Opinion on Therapeutic Patents, vol. 7, No. 6 (1997), pp. 571-588.
Van Seventer et al., "Focal adhesion kinase regulates β1, integrin-dependent T Cell migration through an HEF1 effector pathway", Eur. J. Immunol., vol. 31 (2001), pp. 1417-1427.
Wood et al., "PTK787/ZK 222584, a Novel and Potent Inhibitor of Vascular Endothelial Growth Factor Receptor Tyrosine Kinases, Impairs Vascular Endothelial Growth Factor-induced Responses and Tumor Growth after Oral Administration", Cancer Res., vol. 60 (2000), pp. 2178-2189.

* cited by examiner

2,4-DIAMINOPYRIMIDINE DERIVATIVES

CROSS-REFERENCE TO RELATED PATENT APPLICATIONS

This application is a Divisional of U.S. application Ser. No. 10/507,060, filed Jun. 13, 2005, which is the National Stage of International Application No. PCT/EP03/02710, filed Mar. 14, 2003, which is based upon and claims the benefit of priority from prior United Kingdom Patent Application No. 02062156, filed Mar. 15, 2002, the entire contents of all of which are incorporated herein by reference in their entirety.

The present invention relates to pyrimidine derivatives, to processes for their production, their use as pharmaceuticals and to pharmaceutical compositions comprising them.

More particularly the present invention provides in a first aspect, a compound of formula I

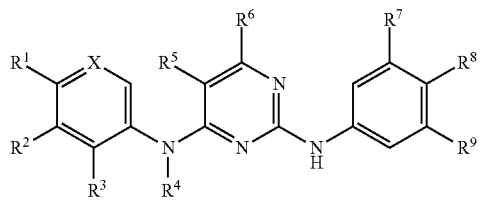

wherein
X is =CR$^0$— or =N—;
each of R$^0$, R$^1$, R$^2$, R$^3$ and R$^4$ independently is hydrogen; hydroxy; $C_1$-$C_8$alkyl; $C_2$-$C_8$alkenyl; $C_3$-$C_8$cycloalkyl; $C_3$-$C_8$cycloalkyl-$C_1$-$C_8$alkyl; hydroxy$C_1$-$C_8$alkyl; $C_1$-$C_8$alkoxy$C_1$-$C_8$alkyl; hydroxy$C_1$-$C_8$alkoxy$C_1$-$C_8$alkyl; aryl$C_1$-$C_8$alkyl which optionally may be substituted on the ring by hydroxy, $C_1$-$C_8$alkoxy, carboxy or $C_1$-$C_8$alkoxycarbonyl;
or R$^3$ and R$^4$ form together with the nitrogen and carbon atoms to which they are attached a 5 to 10 membered heterocyclic ring and comprising additionally 1, 2 or 3 heteroatoms selected from N, O and S;
or each of R$^1$, R$^2$ and R$^3$, independently, is halogen; halo-$C_1$-$C_8$alkyl; $C_1$-$C_8$alkoxy; halo-$C_1$-$C_8$alkoxy; hydroxy$C_1$-$C_8$alkoxy; $C_1$-$C_8$alkoxy$C_1$-$C_8$alkoxy; aryl; aryl$C_1$-$C_8$alkoxy; heteroaryl; heteroaryl-$C_1$-$C_a$alkyl; 5 to 10 membered heterocyclic ring; nitro; carboxy; $C_2$-$C_8$alkoxycarbonyl; $C_2$-$C_8$alkylcarbonyl; —N($C_1$-$C_8$alkyl)C(O)$C_1$-$C_8$alkyl; —N(R$^{10}$)R$^{11}$; —CON(R$^{10}$)R$^{11}$; —SO$_2$N(R$^{10}$)R$^{11}$; or —$C_1$-$C_4$-alkylene-SO$_2$N(R$^{10}$)R$^{11}$;
wherein each of R$^{10}$ and R$^{11}$ independently is hydrogen; hydroxy; $C_1$-$C_8$alkyl; $C_2$-$C_8$alkenyl; $C_3$-$C_8$cycloalkyl; $C_3$-$C_8$cycloalkyl-$C_1$-$C_8$alkyl; $C_1$-$C_8$alkoxy$C_1$-$C_8$alkyl; hydroxy$C_1$-$C_8$alkoxy$C_1$-$C_8$alkyl; hydroxy$C_1$-$C_8$alkyl; ($C_1$-$C_8$alkyl)-carbonyl; aryl$C_1$-$C_8$alkyl which optionally may be substituted on the ring by hydroxy, $C_1$-$C_8$alkoxy, carboxy or $C_2$-$C_8$alkoxycarbonyl; or 5 to 10 membered heterocyclic ring;
or R$^1$ and R$^2$ form together with the C-atoms to which they are attached aryl or a 5 to 10 membered heteroaryl residue comprising one or two heteroatoms selected from N, O and S; or
each of R$^5$ and R$^6$ independently is hydrogen; halogen; cyano; $C_1$-$C_8$alkyl; halo-$C_1$-$C_8$alkyl; $C_2$-$C_8$alkenyl; $C_2$-$C_8$alkynyl; $C_3$-$C_8$cycloalkyl; $C_3$-$C_8$cycloalkyl$C_1$-$C_8$alkyl; $C_5$-$C_{10}$aryl$C_1$-$C_8$alkyl;

each of R$^7$, R$^8$ and R$^9$ is independently hydrogen; hydroxy; $C_1$-$C_8$alkyl; $C_2$-$C_8$alkenyl; halo-$C_1$-$C_8$alkyl; $C_1$-$C_8$alkoxy; $C_3$-$C_8$cycloalkyl; $C_3$-$C_8$cycloalkyl$C_1$-$C_8$alkyl; aryl$C_1$-$C_8$alkyl; —Y—R$^{12}$ wherein Y is a direct bond or O and R$^{12}$ is a substituted or unsubstituted 5, 6 or 7 membered heterocyclic ring comprising 1, 2 or 3 heteroatoms selected from N, O and S; carboxy; ($C_1$-$C_8$alkoxy)-carbonyl; —N($C_{1-8}$alkyl)-CO—NR$^{10}$R$^{11}$; —CONR$^{10}$R$^{11}$; —N(R$^{10}$)(R$^{11}$); —SO$_2$N(R$^{10}$)R$^{11}$; or R$^7$ and R$^8$ or R$^8$ and R$^9$, respectively form together with the carbon atoms to which they are attached, a 5 or 6 membered heteroaryl comprising 1, 2 or 3 heteroatoms selected from N, O and S; or a 5 or 6 membered carbocyclic ring.
in free form or salt form.

Any aryl may be phenyl, naphthyl or 1,2,3,4-tetrahydronaphthyl, preferably phenyl. Heteroaryl is an aromatic heterocyclic ring, e.g. a 5 or 6 membered aromatic heterocyclic ring, optionally condensed to 1 or 2 benzene rings and/or to a further heterocylic ring.

Any heterocyclic ring may be saturated or unsaturated and optionally condensed to 1 or 2 benzene rings and/or to a further heterocyclic ring.

Examples of heterocyclic rings or heteroaryl include e.g. morpholinyl, piperazinyl, piperidyl, pyrrolidinyl, pyridyl, purinyl, pyrimidinyl, N-methyl-aza-cycloheptan-4-yl, indolyl, quinolinyl, isoquinolinyl, 1,2,3,4-tetrahydroquinolinyl, benzothiazolyl, thiazolyl, imidazolyl, benzimidazolyl, benzoxadiazolyl, benzotriazolyl, indanyl, oxadiazolyl, pyrazolyl, triazolyl, and tetrazolyl. Preferred heterocyclic rings or heteroaryl are morpholinyl, piperazinyl, piperidyl, pyrrolidinyl, pyridyl, N-methyl-aza-cycloheptan-4-yl, thiazolyl, imidazolyl and tetrazolyl.

When R$^7$ and R$^8$ or R$^8$ and R$^9$ form together with the carbon atoms to which they are attached a 5 or 6 membered carbocyclic ring, this may preferably be cyclopentyl or cyclohexyl.

Halo-alkyl is alkyl wherein one or more H are replaced by halogen, e.g. CF$_3$.

Any alkyl or alkyl moiety may be linear or branched. $C_{1-8}$alkyl is preferably $C_{1-4}$alkyl. $C_{1-8}$alkoxy is preferably $C_{1-4}$alkoxy. Any alkyl, alkoxy, alkenyl, cycloalkyl, heterocyclic ring, aryl or heteroaryl may be, unless otherwise stated, unsubstituted or substituted by one or more substituents selected from halogen; OH; $C_1$-$C_8$alkyl; $C_1$-$C_8$alkoxy; nitro; cyano; COOH; carbamoyl; C(NH$_2$)=NOH; —N(R$^{10}$)R$^{11}$; $C_3$-$C_6$cycloalkyl; 3 to 7 membered heterocyclic ring; phenyl; phenyl-$C_{1-4}$alkyl; 5 or 6 membered heteroaryl. When alkyl, alkoxy or alkenyl is substituted, the substituent is preferably on the terminal C atom. When the heterocyclic ring or heteroaryl is substituted, e.g. as disclosed above, this may be on one or more ring carbon atoms and/or ring nitrogen atom when present. Examples of a substituent on a ring nitrogen atom are e.g. $C_{1-8}$alkyl, carbamoyl, —C(NH$_2$)=NOH, —NR$^{10}$R$^{11}$, $C_{3-6}$cycloalkyl or phenyl-$C_{1-4}$alkyl, preferably $C_{1-8}$alkyl, $C_{3-6}$cycloalkyl or phenyl-$C_{1-4}$alkyl.

Preferably substituted alkyl or alkoxy as R$_7$ is alkyl or alkoxy substituted on the terminal C atom by OH, $C_{1-4}$alkoxy or a heterocyclic ring. When R$^{10}$ or R$^{11}$ is a 5 to 10 membered heterocyclic ring, it may be e.g. thiazolyl.

Halogen may be F, Cl, Br, or I.

Preferably at most one of R$^1$, R$^2$ or R$^3$ is CONR$^{10}$R$^{11}$ or SO$_2$NR$^{10}$R$^{11}$, more preferably SO$_2$NR$^{10}$R$^{11}$.

The compounds of the invention may exist in free form or in salt form, e.g. addition salts with e.g. organic or inorganic acids, for example trifluoroacetic acid or hydrochloride acid, or salts obtainable when they comprise a carboxy group, e.g. with a base, for example alkali salts such as sodium, potassium, or substituted or unsubstituted ammonium salts.

In formula I the following significances are preferred independently, collectively or in any combination or sub-combination:

(a) X is =CR⁰;
(b) $R^0$ is hydrogen; halogen, e.g. Cl; $C_1$-$C_4$alkyl, e.g. methyl or ethyl; $C_{1-4}$alkoxy, e.g. methoxy; preferably hydrogen;
(c) $R^1$ is hydrogen; halogen, e.g. Cl or F; OH; $C_1$-$C_8$alkyl, e.g. methyl or ethyl; substituted $C_{1-8}$alkyl, e.g. terminally OH substituted $C_{1-8}$alkyl; —SO₂N($R^{10}$)$R^{11}$; —N($C_{1-4}$alkyl)C(O)$C_{1-4}$alkyl; a 5 or 6 membered heterocyclic ring optionally substituted on a ring N atom (when possible); $C_1$-$C_8$alkoxy, e.g. methoxy; aryl, e.g. phenyl; or form together with $R^2$ and the C-atoms to which $R^1$ and $R^2$ are attached 5 to 10 membered aryl or heteroaryl, the latter comprising 1 or 2 nitrogen atoms;
(d) $R^2$ is hydrogen; hydroxy; $C_1$-$C_8$alkyl, e.g. methyl or ethyl; substituted $C_{1-8}$alkyl, e.g. terminally OH— or $C_{1-4}$-alkoxy substituted $C_{1-8}$alkyl; $C_{1-8}$alkoxy; $C_1$-$C_4$alkoxy$C_1$-$C_8$alkoxy; —CON($R^{10}$)$R^{11}$, —SO₂N($R^{10}$)$R^{11}$; or forms together with $R^1$ and the C-atoms to which $R^1$ and $R^2$ are attached a 5 to 10 membered aryl or heteroaryl, the latter comprising 1 or 2 nitrogen atoms;
(e) $R^3$ is hydrogen; halogen, e.g. Cl, Br; hydroxy; $C_1$-$C_8$alkyl, e.g. methyl or ethyl; substituted $C_{1-8}$alkyl, e.g. terminally OH substituted $C_{1-8}$alkyl; carboxy; CONR¹⁰R¹¹; —SO₂N($R^{10}$)$R^{11}$; a 5 or 6 membered heterocyclic ring optionally substituted on a ring nitrogen atom (when possible); or forms together with $R^4$ and the N and C atoms to which $R^3$ and $R^4$ are attached a 6 membered heterocyclic ring;
(f) $R^4$ is hydrogen; or forms together with $R^3$ and the N and C atoms to which $R^3$ and $R^4$ are attached a 6 membered heterocyclic ring; preferably hydrogen;
(g) $R^5$ is hydrogen; halogen; $C_{1-4}$alkyl; or $CF_3$;
(h) $R^6$ is hydrogen;
(i) $R^7$ is hydrogen; hydroxy; $C_{1-4}$alkyl; substituted $C_{1-4}$alkyl, e.g. terminally OH substituted $C_{1-4}$alkyl; $C_{1-8}$alkoxy; substituted $C_{1-8}$alkoxy, e.g. terminally substituted by OH, $C_{1-4}$alkoxy or a heterocyclic ring; NR¹⁰R¹¹; —SO₂N($R^{10}$)$R^{11}$; —Y—$R^{12}$; $CF_3$; or $R^7$ forms together with $R^8$ and the C-atoms to which $R^7$ and $R^8$ are attached a 5 membered heteroaryl residue, e.g. bridged by —NH—CH=CH—, —CH=CH—NH—, —NH—N=CH—, —CH=N—NH—, —NH—N=N— or —N=N—NH—;
(k) $R^8$ is hydrogen; hydroxy; $C_{1-4}$alkoxy; carboxy; a 5 or 6 membered heterocyclic ring optionally substituted on a ring C or N atom; N($C_{1-4}$alkyl)-CO—NR¹⁰R¹¹; or forms with $R^7$ or $R^9$ and the C-atoms to which $R^7$ and $R^8$ or W and $R^9$, respectively, are attached a 5 membered heteroaryl residue, e.g. bridged by —NH—CH=CH—, —CH=CH—NH—, —NH—N=CH—, —CH=N—NH—, —NH—N=N— or —N=N—NH—;
(l) $R^9$ is hydrogen; $C_{1-4}$alkoxy; NR¹⁰R¹¹; or forms with $R^8$ and the C atoms to which $R^8$ and $R^9$ are attached a 5 membered heteroaryl, e.g. bridged by —NH—CH=CH—, —CH=CH—NH—, —NH—N=CH—, —CH=N—NH—, —NH—N=N— or —N=N—NH—;
(m) one of $R^{10}$ and $R^{11}$, independently, is hydrogen or $C_{1-4}$alkyl and the other is hydrogen; OH; $C_{1-8}$alkyl, substituted $C_{1-8}$alkyl, e.g. terminally substituted by OH, $C_{3-6}$cycloalkyl or a heterocyclic ring; $C_{2-8}$alkenyl; $C_{3-8}$cycloalkyl; hydroxy$C_{1-8}$alkoxy$C_{1-8}$alkyl; or a 5 membered heterocyclic ring.

$R^3$ is preferably SO₂NR¹⁰R¹¹.

The present invention also provides a process for the production of a compound of formula I, comprising reacting a compound of formula II

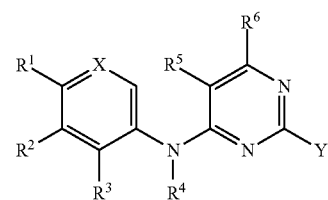

wherein $R^1$, $R^2$, $R^3$, $R^4$, $R^5$, $R^6$ and X are as defined above, and Y is a leaving group, preferably halogen such as bromide, iodine, or in particular chloride;

with a compound of formula III

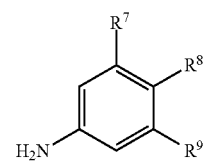

wherein $R^7$, $R^8$ and $R^9$ are as defined above;

and recovering the resulting compound of formula I in free or in form of a salt, and, where required, converting the compound of formula I obtained in free form into the desired salt form, or vice versa.

The process may be performed according to methods known in the art, e.g. as described in examples 1 to 4.

The compound of formula II used as starting materials may be obtained by reacting a compound of formula IV

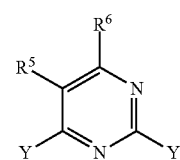

with a compound of formula V

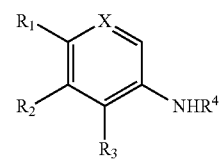

wherein $R^1$, $R^2$, $R^3$, $R^4$, $R^5$, $R^6$, Y and X are as defined above.

The compounds of formula IV and V are known or may be produced in accordance with known procedures.

The following examples illustrate the invention without any limitation.

The following abbreviations are employed: APC=allophycocyanine, BINAP=2,2'-bis(diphenylphosphino)-1,1'-binaphthyl, cDNA=complementary DNA, DCM=dichloromethane, DIAD=diisopropyl azodicarboxylate, DMAP=4-dimethylaminopyridine, DMF=dimethylformamide, DMSO=dimethylsulfoxide, DMF=dimethylformamide; Pmc=2,2,5,7,8-pentamethylchroman; tBu=tert.-butyl; DIPCDI=N,N'-diisopropylcarbodiimid; DTT=1,4-dithio-D,L-treitol, DNA=deoxyribonucleic acid, EDTA=ethylenediaminetetraacetic acid, Lck=lymphoid T-cell protein tyrosine kinase, LAT-11=linker for activation of T cell, RT=room temperature; RT-PCR=reverse transcription polymerase chain reaction, MS=molecular ion (e.g. M+H$^{1+}$) determined by electrospray mass spectroscopy; Eu=europium; ZAP-70=zeta chain-associated protein of 70 kD; Syk=p72syk protein tyrosine kinase; SA=streptavidin.

EXAMPLE 1

2-[2-(1H-Indazol-6-ylamino)-pyrimidin-4-ylamino]-benzenesulfonamide

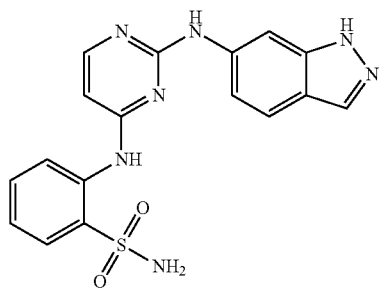 [SMILES: NS(=O)(=O)c1ccccc1Nc1ccnc(Nc2ccc3cn[nH]c3c2)n1]

(a) 2-(2-Chloro-pyrimidin-4-ylamino)-benzenesulfonamide: To a suspension of 8.52 g (49.47 mmol) 2-aminobenzenesulfonamide in 200 ml isopropanol is added 22.1 g (148.42 mmol, 3 equivalent) 2,4-dichloropyrimidine and 20 ml 10 M hydrochloric acid (200 mmol, 4 equivalent). The suspension is stirred at 60° C. for 2 h 15 min. The reaction mixture is diluted with 2 l ethyl acetate and 500 ml water is added. The pH is adjusted to 8-9 by addition of sodium bicarbonate. The layers are separated and the aqueous layer is reextracted with 500 ml ethyl acetate. The organic layers are dried with sodium sulfate, filtered and evaporated to a volume of 300 ml. A crystalline precipitate is formed and removed by filtration (side product). The filtrate is evaporated to 100 ml whereupon the product crystallizes to give 2-(2-chloro-pyrimidin-4-ylamino)-benzenesulfonamide (97% purity by HPLC). The mother liquor of this crystallisation is further purified by column chromatography and crystallisation to give further 2-(2-chloro-pyrimidin-4-ylamino)-benzenesulfonamide.

(b) 2-[2-(1H-Indazol-6-ylamino)-pyrimidin-4-ylamino]-benzenesulfonamide: To a suspension of 7.25 g (25.46 mmol) 2-(2-Chloro-pyrimidin-4-ylamino)-benzenesulfonamide and 4.07 g (30.55 mmol, 1.2 equivalent) 6-aminoindazole in 400 ml isopropanol is added 13 ml conc. HCl* (130 mmol, 5 equivalent). The suspension is refluxed for 4 h 30 min. The reaction mixture is diluted with 1.5 l ethyl acetate and 1 l water is added. The pH is adjusted to 8-9 by addition of sodium bicarbonate. The layers are separated and the aqueous layer is re-extracted with 500 ml ethyl acetate. The organic layers are dried with sodium sulfate, filtered and evaporated to a volume of 300 ml. A crystalline precipitate (1.01 g) is formed and removed by filtration (side product). The filtrate is purified by chromatography on 200 g silica gel eluting with ethyl acetate/methanol 95/5 v/v. Upon evaporation crystals are formed which are filtered to give the title compound.

$^1$H NMR (400 MHz, DMSO-d$_6$): δ9.42 (s, 1H), 8.34 (d, 1h), 8.28 (d, 1H), 8.27 (s, 1H), 7.93 (s, 1H, 7.88 (d, 1H), 7.62 (m, 2H), 7.32 (d, 1H), 7.24 (t, 1H), 6.40 (d, 1H).

MS m/z (%): 382 (M+H, 100);

EXAMPLE 2

2-[2-(3,4,5-Trimethoxy-phenylamino)-pyrimidin-4-ylamino]-benzenesulfonamide

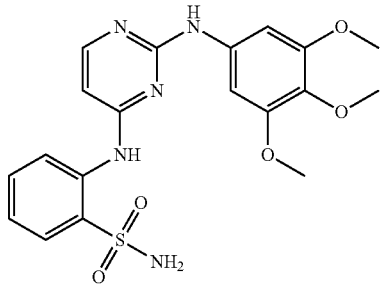

The title compound is prepared from 2-(2-chloro-pyrimidin-4-ylamino)-benzenesulfonamide as described in Example 1 using 3,4,5-Trimethoxy-phenylamine instead of 6-aminoindazole in step (b).

$^1$H NMR (400 MHz, DMSO-d$_6$): δ9.18 (s, 1H), 8.22 (d, 1H), 8.17 (d, 1H), 7.89 (d, 1H), 7.55 (t, 1H), 7.25 (t, 1H), 7.14 (s, 2H), 6.40 (d, 1H), 3.69 (s, 6H), 3.62 (s, 3H). MS m/z (%): 432 (M+H, 100);

EXAMPLE 3

2-methyl-6-[2-(3,4,5-Trimethoxy-phenylamino)-pyrimidin-4-ylamino]-benzenesulfonamide

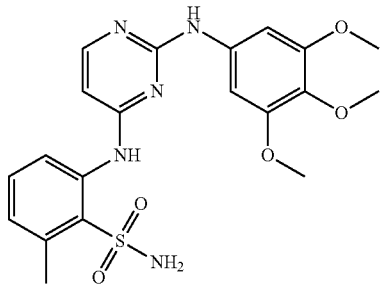 [SMILES: COc1cc(Nc2nccc(Nc3cccc(C)c3S(N)(=O)=O)n2)cc(OC)c1OC]

The title compound is prepared as described in Example 1 with the difference that in step (a) 2-amino-6-methyl-benzenesulfonamide is used instead of 2-aminobenzenesulfonamide. 2-Amino-6-methyl-benzenesulfonamide may be prepared as described by Girard, Y et al.; *J. J. Chem. Soc. Perkin Trans. I* 1979, 4, 1043-1047: Under an atmosphere of nitrogen m-toluidin (32.1 g, 32.5 ml, 0.30 mmol) is added dropwise to a solution of chlorosulfonyl isocyanate (51.3 ml, 83.6 g, 0.59 mmol) in nitroethane (400 ml) at −55-49° C. The cold bath is removed and the mixture allowed to warm to −8° C., whereupon aluminium chloride (51 g, 0.38 mmol) is added. Heating the mixture to 100° C. for 20 min forms a clear brown solution, which is cooled to RT and poured on ice. After filtration, washing with ice water and diethyl ether the precipitate is collected and dissolved in dioxane (300 ml). Water (1000 ml) and conc. HCl (1500 ml) are added to form a suspension, which is heated to 120° C. for 18 h. After cooling to RT the clear brown solution is washed with diethyl ether/hexane (1400 ml, 1/1 v/v) and adjusted to pH=8 by addition of sodium carbonate. Extraction using ethyl acetate (2×1000 ml), washing of the organic phase with water (500 ml) and brine (500 ml), drying (magnesium sulfate) and concentration yields a brown solid, which is purified by chromatography on silica using methylene chloride/ethanol (100/1 v/v) to yield the desired product as a white solid.

Melting point: 72-75° C. (Propan-2-ol);

$^1$H NMR (400 MHz, DMSO-$d_6$): δ 2.64 (s, 3H, Me), 3.63 (s, 3H, OMe), 3.68 (s, 6H, OMe), 6.31 (d, J=5 Hz, 1H, pyrimidine CH), 7.07 (d, J=8 Hz, 1H, arom. CH), 7.15 (s, 2H, arom. CH), 7.40 (t, J=8 Hz, 1H, arom. CH), 7.65 (s, 2H, SO$_2$NH$_2$), 8.04 (d, J=8 Hz, 1H, arom. CH), 8.12 (d, J=5 Hz, 1H, pyrimidine CH), 9.14 (s, 1H, NH), 9.40 (s, 1H, NH).

MS (ES$^+$)m/z: 446 (MH$^+$), 468 (MNa$^+$)

MS (ES$^-$): 444 (M–H)$^-$

EXAMPLE 4

2-Methoxy-6-[2-(3,4,5-trimethoxy-phenylamino)-pyrimidin-4-ylamino]-benzenesulfonamide

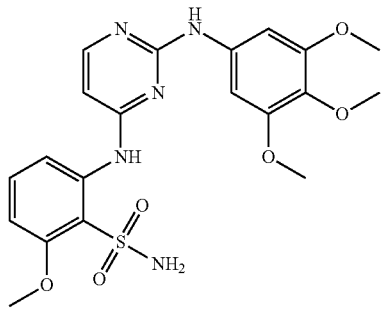 [SMILES: COc1cc(Nc2nccc(Nc3cccc(OC)c3S(N)(=O)=O)n2)cc(OC)c1OC]

The title compound is prepared as described in Example 1 with the difference that in step (a) 2-amino-6-methoxy-benzenesulfonamide is used instead of 2-Amino-6-methyl-benzenesulfonamide.

2-Amino-6-methoxy-benzenesulfonamide may be prepared from 12.3 g of meta-anisidine following an analogous procedure as described in Example 1a. NMR (400 MHz, DMSO-$d_6$): δ3.62 (s, 3H, OMe), 3.69 (s, 6H, OMe), 3.91 (s, 3H, OMe), 6.31 (d, J=5 Hz, 1H, pyrimidine CH), 6.86 (d, J=8 Hz, 1H, arom. CH), 7.12 (s, 2H, arom. CH), 7.43 (t, J=8 Hz, 1H, arom. CH), 8.01 (d, J=8 Hz, 1H, arom. CH), 8.11 (d, J=5 Hz, 1H, pyrimidine CH), 9.18 (s, 1H, NH), 9.79 (br, 1H, NH).

MS (ES$^+$): 462.2 (MH$^+$), 484.2 (MNa$^+$)

MS (ES$^-$): 460.3 (M–H)$^-$

The compounds of formula $X_1$

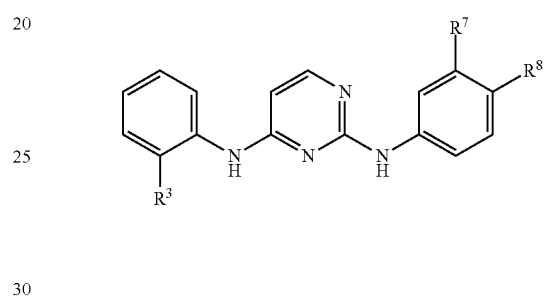

wherein $R^3$, $R^7$ and $R^8$ are as defined in Table 1, may be prepared by following the procedure of Example 1 but using the appropriate starting materials.

TABLE 1

| Example | $R^3$ | $R^7$ | $R^8$ | MS Data *ES+ | *ES− | *EI |
|---|---|---|---|---|---|---|
| 5 | —OH | —O-(1-methyl)-azacyclohept-4-yl | —H | 406 | 404 | |
| 6 | —SO$_2$NH$_2$ | —O-(1-methyl)-azacyclohept-4-yl | —H | 469.3 | | |
| 7 | —SO$_2$NH$_2$ | —O-2-(1-methyl-azacyclopent-2-yl)-ethyl | —H | 469.3 | | |
| 8 | —OH | —O-2-(1-piperidyl)-ethyl | —OCH$_3$ | 436.3 | 434.4 | |
| 9 | —OH | —O-2-(1-methyl-azacyclopent-2-yl)-ethyl | —H | 406 | 404 | |
| 10 | —SO$_2$NH$_2$ | —O—CH$_2$CH$_2$CH$_2$-1-imidazolyl | —OCH$_3$ | 496 | 494 | |
| 11 | —SO$_2$NH$_2$ | —O-2-(1-piperidyl)-ethyl | —OCH$_3$ | 499.2 | 497.3 | |
| 12 | —SO$_2$NH$_2$ | —O—CH$_2$CH$_2$-1-methyl-imidazol-1-yl | —H | 466 | 464 | |
| 13 | —OH | —O-2-[1-(1,2,4-triazolyl)]-ethyl | —H | 390 | 388 | |
| 14 | —OH | —O-2-hydroxyethyl | —OCH$_3$ | 369.4 | 367.3 | |
| 15 | —SO$_2$NH$_2$ | —O-2-hydroxyethyl | —OCH$_3$ | | | 431 |
| 16 | —SO$_2$NH$_2$ | —O—CH$_2$CH$_2$-1-imidazolyl | —OCH$_3$ | | | |
| 17 | —SO$_2$NH$_2$ | —O-2-[1-(1,2,4-triazolyl)]-ethyl | —H | | | 452 |
| 18 | —SO$_2$NH$_2$ | —NH—N=N— | | | 381 | |
| 19 | —SO$_2$NHCH$_3$ | —O—CH$_2$CH$_2$-1-imidazolyl | —OCH$_3$ | 496 | 494 | |
| 20 | —SO$_2$NH$_2$ | —O-2-(1-piperidyl)-ethyl | —H | 469 | 467 | |
| 21 | —SO$_2$NH$_2$ | —O—CH$_2$CH$_2$-1-imidazolyl | —H | 452 | 450 | |
| 22 | —OH | —O-2-(1-piperidyl)-ethyl | —H | 406 | | |
| 23 | —COOH | -4-morpholino | —H | | | |
| 24 | —OH | —O—CH$_2$CH$_2$CH$_2$-1-imidazolyl | —OCH$_3$ | 433 | 431 | |
| 25 | —SO$_2$NHCH$_3$ | —CH=N—NH— | | 396 | 394 | |
| 26 | —SO$_2$NH$_2$ | —O-2-(4-morpholino)ethyl | —H | 471 | 469 | |
| 27 | —SO$_2$NH$_2$ | —OCH$_3$ | —OCH$_3$ | 402 | 400 | |
| 28 | —OH | —O-2-(4-morpholino)ethyl | —H | 408 | 406 | |
| 29 | —SO$_2$NH$_2$ | —CH=N—NH— | | | | 381 |
| 30 | —SO$_2$NHCH$_3$ | —O—CH$_2$CH$_2$-1-imidazolyl | —H | | | |
| 31 | —COOH | amino | —H | 322 | | |
| 32 | —SO$_2$NH$_2$ | —O—CH$_2$CH$_2$CH$_2$-1-imidazolyl | —H | 466.2 | 464.3 | |
| 33 | —COOH | —N(CH$_3$)$_2$ | —H | | | |
| 34 | -5-(1,2,3,4-tetrazolyl) | —NH—C(O)CH$_3$ | —H | 388 | 386 | |
| 35 | —SO$_2$NHCH$_3$ | | —NH—N=CH— | | | |

TABLE 1-continued

| Example | $R^3$ | $R^7$ | $R^8$ | MS Data *ES+ | *ES− | *EI |
|---|---|---|---|---|---|---|
| 36 | —COOH | —OH | —H | | | |
| 37 | —COOH | —H | -4-piperidyl | | | |
| 38 | —COOH | —CH$_2$—OH | —H | | | |
| 39 | —OH | —O—CH$_2$CH$_2$-1-imidazolyl | —OCH3 | | | |
| 40 | —SO$_2$NH—CH$_2$CH$_2$—OH | —O—CH$_2$CH$_2$-1-imidazolyl | —H | 496 | 494 | |
| 41 | —C(O)NH$_2$ | amino | —H | 321 | | |
| 42 | —SO$_2$NH$_2$ | —CH=CH—NH— | | 381 | | |
| 43 | -5-(1,2,3,4-tetrazolyl) | —NHCH$_2$-3-pyridyl | —H | | | 435 |
| 44 | —SO$_2$NH$_2$ | —NH—CH=CH— | | | | 379 |
| 45 | —COOH | —H | -4-morpholino | | | |
| 46 | —COOH | —H | -1-(4-amino)-piperidyl | | | |
| 47 | —SO$_2$NH$_2$ | —OCH$_3$ | —H | 372 | 370 | |
| 48 | —SO$_2$N(CH$_3$)$_2$ | —O—CH$_2$CH$_2$-1-imidazolyl | —H | 480 | 478 | |

The compounds of formula $X_2$

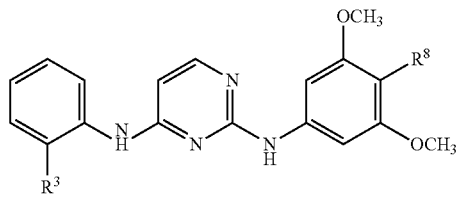

wherein $R^3$ and $R^8$ are as defined in Table 2, may be prepared by following the procedure of Example 1 but using the appropriate starting materials.

TABLE 2

| Example | $R^3$ | $R^8$ | MS Data *ES+ | *ES− |
|---|---|---|---|---|
| 49 | —COOH | —OCH$_3$ | 397 | 395 |
| 50 | —SO$_2$NH$_2$ | —OH | | |
| 51 | —SO$_2$NHCH$_3$ | —OCH$_3$ | | |
| 52 | -5-(1,2,3,4-tetrazolyl) | —OCH$_3$ | 421 | |
| 53 | —SO$_2$NH-cyclopropyl | —OCH$_3$ | 472.2 | 470.3 |

TABLE 2-continued

| Example | $R^3$ | $R^8$ | MS Data *ES+ | *ES− |
|---|---|---|---|---|
| 54 | —C(O)NHOH | —OCH$_3$ | 412 | 410 |
| 55 | —SO$_2$NH—CH$_2$CH$_2$—OH | —OCH$_3$ | 476 | 474 |
| 56 | —SO$_2$N(CH$_3$)$_2$ | —OCH$_3$ | 460.3 | 458.3 |
| 57 | —OH | —OCH$_3$ | 369 | 367 |
| 58 | —SO$_2$NH—CH$_2$CH$_2$CH$_3$ | —OCH$_3$ | 474 | 472 |
| 59 | —CH$_2$OH | —OCH$_3$ | | |
| 60 | —SO$_2$NH$_2$ | —H | 402 | |

The compounds of formula $X_3$

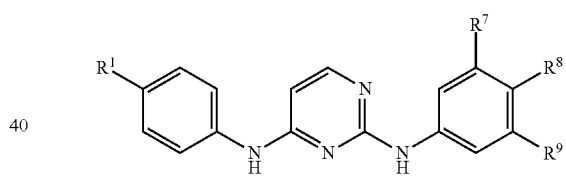

wherein $R^1$, $R^7$, $R^8$ and $R^9$ are as defined in Table 3, may be prepared by following the procedure of Example 1 but using the appropriate starting materials.

TABLE 3

| Example | $R^1$ | $R^7$ | $R^8$ | $R^9$ | MS Data *ES+ | *ES− |
|---|---|---|---|---|---|---|
| 61 | —SO$_2$NH—CH$_2$CH$_2$—O—CH$_2$CH$_2$—OH | —H | —N(CH$_3$)—C(O)CH$_3$ | —H | | |
| 62 | —SO$_2$NH$_2$ | —OCH$_3$ | —OCH$_3$ | —OCH$_3$ | | |
| 63 | —SO$_2$NH$_2$ | —O—CH$_2$CH$_2$-1-imidazolyl | —OCH$_3$ | —H | | |
| 64 | —SO$_2$NH—CH$_2$CH$_2$—O—CH$_2$CH$_2$—OH | —OCH$_3$ | —OCH$_3$ | —OCH$_3$ | 520 | 518 |
| 65 | —N(CH$_3$) C(O)CH$_3$ | —OCH$_3$ | —OCH$_3$ | —OCH$_3$ | 424 | 422 |
| 66 | —CH$_2$CH$_2$—OH | —SO$_2$NH—CH$_2$CH$_2$CH$_2$CH$_3$ | —H | —H | | |
| 67 | —SO$_2$NH$_2$ | —OCH$_3$ | —H | —OCH$_3$ | | |
| 68 | —SO$_2$NH$_2$ | —O—CH$_2$CH$_2$-1-imidazolyl | —H | —H | | |
| 69 | —CH$_2$CH$_2$—OH | —O—CH$_2$CH$_2$-1-imidazolyl | —H | —H | | |
| 70 | —CH$_2$CH$_2$—OH | —OCH$_3$ | —H | —OCH$_3$ | | |
| 71 | —SO$_2$NH$_2$ | —OH | —H | —H | | |
| 72 | —O—CH$_2$CH$_2$—OH | —O—CH$_2$CH$_2$-1-imidazolyl | —H | —H | | |
| 73 | —SO$_2$NH-2-thiazolyl | —OCH$_3$ | —OCH$_3$ | —OCH$_3$ | 515 | 513 |

The compounds of formula $X_4$

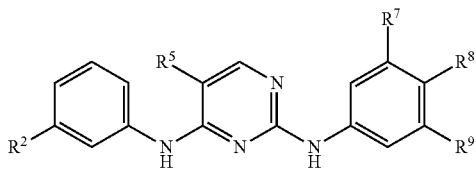

wherein $R^2$, $R^5$, $R^7$, $R^8$ and $R^9$ are as defined in Table 4, may be prepared by following the procedure of Example 1 but using the appropriate starting materials.

TABLE 4

| Example | $R^2$ | $R^5$ | $R^7$ | $R^8$ | $R^9$ | MS Data *ES+ | MS Data *ES− |
|---|---|---|---|---|---|---|---|
| 74 | —SO$_2$NH-2-propenyl | —H | —OCH$_3$ | —OCH$_3$ | —OCH$_3$ | 472 | 470 |
| 75 | —SO$_2$NH$_2$ | —H | —OCH$_3$ | —OCH$_3$ | —OCH$_3$ | | |
| 76 | —OH | —H | —O-(1-methyl)-azacyclohept-4-yl | —H | —H | 406.3 | 404.3 |
| 77 | —OH | —H | —O—CH$_2$CH$_2$—OH | —OCH$_3$ | —H | 369 | 367 |
| 78 | —SO$_2$NH$_2$ | —Br | —OCH$_3$ | —OCH$_3$ | —OCH$_3$ | 510.1/512.1 | 508.1/510.2 |
| 79 | —SO$_2$NH$_2$ | —H | —CH=N—NH— | | —H | 382 | |
| 80 | —SO$_2$NH$_2$ | —CH$_3$ | —OCH$_3$ | —OCH$_3$ | —OCH$_3$ | 446 | 444 |
| 81 | —SO$_2$NH$_2$ | —H | —O—CH$_2$CH$_2$-1-imidazolyl | —OCH$_3$ | —H | 482 | 480 |
| 82 | —OH | —H | —O—CH$_2$CH$_2$-1-piperidyl | —OCH$_3$ | —H | 436.3 | 434.3 |
| 83 | —OH | —H | —O—CH$_2$CH$_2$-1-imidazolyl | —OCH$_3$ | —H | 419 | 417 |
| 84 | —SO$_2$NH$_2$ | —H | —O—CH$_2$CH$_2$-1-imidazolyl | —H | —H | 452 | 450 |
| 85 | —CH$_3$ | —C≡N | —OCH$_3$ | —OCH$_3$ | —OCH$_3$ | 392 | |
| 86 | —SO$_2$NH$_2$ | —H | —NH—N=CH— | | —H | 382 | |
| 87 | —OH | —H | —OCH$_3$ | —OCH$_3$ | —OCH$_3$ | 369 | 367 |
| 88 | —SO$_2$NHCH$_3$ | —CH$_3$ | —OCH$_3$ | —OCH$_3$ | —OCH$_3$ | 460 | 458 |
| 89 | —OH | —H | —OH | —COOH | —OCH$_3$ | | |
| 90 | —OH | —H | —O—CH$_2$CH$_2$-1-piperidyl | —H | —H | 406 | 404 |
| 91 | —SO$_2$NH-2-propenyl | —H | —O—CH$_2$CH$_2$-1-imidazolyl | —H | —H | 492.3 | 490.3 |
| 92 | —SO$_2$NH$_2$ | —Br | —O—CH$_2$CH$_2$-1-(1-methyl)-imidazolyl | —H | —H | 544.1/546 | 542/544.2 |
| 93 | —SO$_2$NH$_2$ | —H | —O—CH$_2$CH$_2$—OH | —OCH$_3$ | —H | | |
| 94 | —OH | —H | —O-(1-methyl)-azacyclopent-2-yl | —H | —H | | |
| 95 | —OH | —H | —O—CH$_2$CH$_2$-1-imidazolyl | —H | —H | 389 | 387 |
| 96 | —OH | —H | —O—CH$_2$CH$_2$CH$_2$-1-imidazolyl | —OCH$_3$ | —H | 433.4 | 431.4 |
| 97 | —SO$_2$NH$_2$ | —H | —OCH$_3$ | —H | —OCH$_3$ | | |
| 98 | —OH | —H | —OCH$_3$ | —OCH$_3$ | —H | 339 | 337 |
| 99 | —SO$_2$NHCH$_2$—CH$_2$CH$_2$CH$_3$ | —H | —OCH$_3$ | —OCH$_3$ | —OCH$_3$ | 488 | 486 |
| 100 | —SO$_2$NH—CH$_3$ | —CH$_3$ | —O—CH$_2$CH$_2$-1-imidazolyl | —OCH$_3$ | —H | 510 | 508 |
| 101 | —SO$_2$NHCH$_2$—CH$_2$CH$_2$CH$_3$ | —H | —O—CH$_2$CH$_2$-1-imidazolyl | —H | —H | 08 | 506 |
| 102 | —OH | —H | —O—CH$_2$CH$_2$-4-morpholino | —H | —H | 408 | |
| 103 | —OH | —H | —NH—N=CH— | | —H | 319 | 317 |
| 104 | —OH | —H | —CHN—NH— | | —H | 319 | 317 |
| 105 | —OH | —H | —O—CH$_2$CH$_2$-1-imidazolyl | —H | —H | | |
| 106 | —SO$_2$NH—CH$_3$ | —CH$_2$—CH$_3$ | —OCH$_3$ | —OCH$_3$ | —OCH$_3$ | 474.3 | 472.3 |
| 107 | —SO$_2$NH$_2$ | —H | —OCH$_3$ | —OCH$_3$ | —OCH$_3$ | | |

The compounds of formula $X_5$

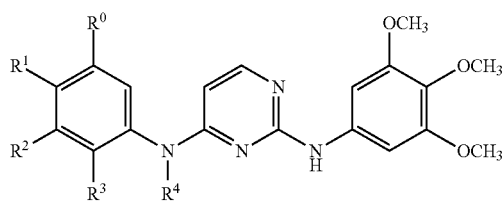

wherein $R^0$, $R^1$, $R^2$, $R^3$ and $R^4$ are as defined in Table 5, may be prepared by following the procedure of Example 1 but using the appropriate starting materials.

TABLE 5

| Example | $R^0$ | $R^1$ | $R^2$ | $R^3$ | $R^4$ | MS Data *ES+ | *ES− |
|---|---|---|---|---|---|---|---|
| 108 | —H | —OCH$_3$ | —OH | —H | —H | | |
| 109 | —H | nitro | —H | —OH | —H | 414 | 412 |
| 110 | —H | —N=CH—CH=CH— | | —H | —H | | |
| 111 | —H | —CH=N—NH— | | —H | —H | 393 | 391 |
| 112 | —H | —NH—N=CH— | | —H | —H | 393 | |
| 113 | —H | —H | —OH | —CH$_2$CH$_2$CH$_2$— | | 409 | 407 |
| 114 | —CH$_3$ | —H | —CH$_3$ | —OH | —H | 397 | |
| 115 | —H | phenyl | —H | —SO$_2$NH$_2$ | —H | 508 | 506 |
| 116 | —CH$_3$ | —H | —H | —SO$_2$NH$_2$ | —H | 446 | 444 |

The compounds of formula $X_6$

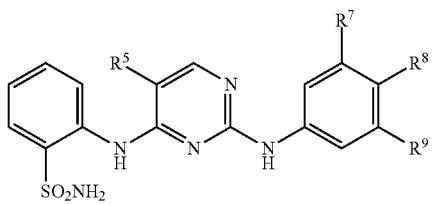

wherein $R^5$, $R^7$, $R^8$ and $R^9$ are as defined in Table 6, may be prepared by following the procedure of Example 1 but using the appropriate starting materials.

TABLE 6

| Example | $R^5$ | $R^7$ | $R^8$ | $R^9$ | *ES+ | *ES− |
|---|---|---|---|---|---|---|
| 117 | —CH$_3$ | —O—CH$_2$CH$_2$-1-imidazolyl | —H | —H | 466 | |
| 118 | —CH$_2$CH$_3$ | —OCH$_3$ | —OCH$_3$ | —OCH$_3$ | 460 | 458 |
| 119 | —Br | —NH—N=CH— | | —H | 461 | |
| 120 | —CH$_3$ | —O—CH$_2$CH$_2$-1-imidazolyl | —OCH$_3$ | —H | 496 | |
| 121 | —CH$_3$ | —OCH$_3$ | —OCH$_3$ | —OCH$_3$ | 446 | |
| 122 | —CH$_3$ | —N=N—NH— | | —H | 397.2 | 395.2 |
| 123 | —CH$_3$ | —O—CH$_2$CH$_2$-1-methyl-imidazol-1-yl | —H | —H | 480 | |
| 124 | —Br | —CH=N—NH— | | —H | 461.3 | 458.1/460 |
| 125 | —CH$_3$ | —NH—N=CH— | | —H | 396 | |
| 126 | —Br | —OCH$_2$CH$_2$-(4-methyl-piperazin-1-yl) | —H | —H | 562/564 | 560/562 |

The compounds of formula $X_7$

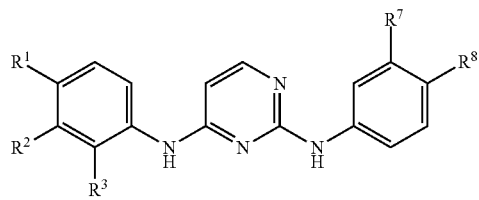

wherein $R^1$, $R^2$, $R^3$, $R^7$ and $R^8$ are as defined in Table 7, may be prepared by following the procedure of Example 1 but using the appropriate starting materials.

TABLE 7

| Ex | $R^1$ | $R^2$ | $R^3$ | $R^7$ | $R^8$ | *ES+ | *ES− |
|---|---|---|---|---|---|---|---|
| 127 | —OCH$_3$ | —OH | —H | —OH | —OCH$_3$ | | |
| 128 | —H | —CH$_3$ | —SO$_2$NH$_2$ | —O—CH$_2$CH$_2$-1-imidazolyl | —H | 466 | 464 |

TABLE 7-continued

| Ex | $R^1$ | $R^2$ | $R^3$ | $R^7$ | $R^8$ | *ES+ | *ES- |
|---|---|---|---|---|---|---|---|
| 129 | —OCH$_3$ | —OH | —H | —O—CH$_2$CH$_2$-1-imidazolyl | —OCH$_3$ | | |
| 130 | —OCH$_3$ | —OH | —H | —O—CH$_2$CH$_2$—OH | —OCH$_3$ | 399 | 397 |
| 131 | —OCH$_3$ | —OH | —H | —O-(1-methyl-azacyclohept-4-yl) | —H | 436 | |
| 132 | —CH$_3$ | —H | —SO$_2$NH$_2$ | —O—CH$_2$CH$_2$-1-imidazolyl | —H | 466 | 464 |
| 133 | —OCH$_3$ | —OH | —H | —O—CH$_2$CH$_2$-(1-methyl)-azacyclopent-2-yl | —H | 436 | 434 |
| 134 | —OCH$_3$ | —OH | —H | —CF$_3$ | —H | | |
| 135 | —N═CH—CH═CH— | | —H | —O—CH$_2$CH$_2$-1-imidazolyl | —OCH$_3$ | | |
| 136 | —OCH$_3$ | —OH | —H | —O—CH$_2$CH$_2$CH$_2$-1-imidazolyl | —OCH$_3$ | 463 | 461 |
| 137 | —OCH$_3$ | —OH | —H | —O—CH$_2$CH$_2$-1-piperidyl | —OCH$_3$ | 466.4 | 464.4 |
| 138 | —CH═N—NH— | | —H | —NH—N═CH— | | | |
| 139 | —CH═N—NH— | | | —CH—N═NH— | | | |
| 140 | —OCH$_3$ | —OH | —H | —O—CH$_2$CH$_2$-1-piperidyl | —H | 436 | 434 |
| 141 | —H | —OCH$_3$ | —SO$_2$NH$_2$ | —O—CH$_2$CH$_2$-1-pyrrolidinyl | —H | 485.3 | 483.3 |
| 142 | —H | —OCH$_3$ | —SO$_2$NH$_2$ | —O—CH$_2$CH$_2$-1-pyrrolidinyl | —CH$_3$ | 499.2 | 497.3 |
| 143 | —H | —OCH$_3$ | —SO$_2$NH$_2$ | —O—CH$_2$CH$_2$CH$_2$-morpholino | —OCH$_3$ | 545.2 | 545.3 |
| 144 | —H | —OCH(CH$_3$)$_2$ | —SO$_2$NH$_2$ | —O—CH$_2$CH$_2$-(4-methyl-piperazin-1-yl) | —OCH$_3$ | 572.2 | 570.3 |
| 145 | —H | —OCH$_3$ | —SO$_2$NH$_2$ | —O—CH$_2$CH$_2$-1-piperidinyl | —H | 499.2 | 497.3 |
| 146 | —CH$_3$ | —OCH$_3$ | —SO$_2$NH$_2$ | —O—CH$_2$CH$_2$CH$_2$-1-pyrrolidinyl | —OCH$_3$ | 543.2 | |
| 147 | —CH$_3$ | —OCH$_3$ | —SO$_2$NH$_2$ | —O—CH$_2$CH$_2$CH$_2$-1-pyrrolidinyl | —H | 513.2 | 511.2 |
| 148 | —H | —OCH(CH$_3$)$_2$ | —SO$_2$NH$_2$ | —O—CH$_2$CH$_2$-1-piperidinyl | —H | 527.2 | 525.3 |
| 149 | —H | —CH$_3$ | —SO$_2$NH$_2$ | —N(CH$_3$)$_2$ | —OCH$_3$ | 429.3 | 427.3 |
| 150 | —CH$_3$ | —CH$_3$ | —SO$_2$NH$_2$ | —O—CH$_2$CH$_2$CH$_2$-1-pyrrolidinyl | —OCH$_3$ | 527.2 | 525.3 |
| 151 | —OCH$_3$ | —H | —SO$_2$NH$_2$ | —O—CH$_2$CH$_2$CH$_2$-1-pyrrolidinyl | —OCH$_3$ | 529.2 | 527.3 |
| 152 | —H | —F | —SO$_2$NH$_2$ | —N(CH$_3$)$_2$ | —OCH$_3$ | 433.1 | |
| 153 | —H | —CH$_3$ | —SO$_2$NH$_2$ | —O—CH$_2$CH$_2$-(1-methyl-pyrrolidin-2-yl) | —H | | |
| 154 | —H | —OCH$_3$ | —SO$_2$NH$_2$ | —O—CH$_2$CH$_2$—OH | —H | 432.2 | 430.2 |
| 155 | —H | —CH$_3$ | —SO$_2$NH$_2$ | —O—CH$_2$CH$_2$-(1-methyl-pyrrolidin-2-yl) | —OCH$_3$ | 513.2 | 511.3 |
| 156 | —OCH$_3$ | —H | —SO$_2$NH$_2$ | —O—CH$_2$CH$_2$-1-piperidinyl | —H | 499.2 | 497.3 |
| 157 | —OCH$_3$ | —H | —SO$_2$NH$_2$ | —O—CH$_2$CH$_2$-1-pyrrolidinyl | —OCH$_3$ | 515.2 | 513.2 |
| 158 | —H | —CH$_3$ | —SO$_2$NH$_2$ | —O—CH$_2$CH$_2$—OH | —OCH$_3$ | 446.2 | 444.2 |
| 159 | —OC$_2$H$_5$ | —H | —SO$_2$NH$_2$ | —O—CH$_2$CH$_2$-1-pyrrolidinyl | —CH$_3$ | 513.3 | 511.3 |
| 160 | —OCH$_3$ | —OCH$_3$ | —SO$_2$NH$_2$ | —O—CH$_2$CH$_2$-(4-methyl-piperazin-1-yl) | —OCH$_3$ | 574.2 | 572.2 |
| 161 | —H | —Cl | —SO$_2$NH$_2$ | -(4-methyl-piperazin-1-yl) | —H | 474.5 | 472.5 |
| 162 | —H | —CH$_3$ | —SO$_2$NH$_2$ | —O—CH$_2$CH$_2$-(4-cyclopentyl-piperazin-1-yl) | —H | 552.3 | 550.3 |
| 163 | —CH═CH—CH═CH— | | —SO$_2$NH$_2$ | -(4-methyl-piperazin-1-yl) | —H | 490.5 | 488.4 |
| 164 | —H | —H | —SO$_2$NH$_2$ | —O—CH$_2$CH$_2$-piperazin-1-yl | —H | 470.2 | 468.3 |
| 165 | —H | —OCH$_3$ | —SO$_2$NH$_2$ | —H | —OCH$_3$ | 402.2 | 400.2 |
| 166 | —H | —OCH$_3$ | —SO$_2$NH$_2$ | —O—CH$_2$CH$_2$-(4-benzyl-piperazin-1-yl) | —H | 590.3 | 588.3 |
| 167 | —CH$_3$ | —H | —SO$_2$NH$_2$ | —O—CH$_2$CH$_2$-1-pyrrolidinyl | —H | 469.2 | 467.3 |
| 168 | —Br | —H | —SO$_2$NH$_2$ | —O—CH$_2$CH$_2$-1-piperidinyl | —H | 549.1 | 547.2 |

The compounds of formula X$_8$

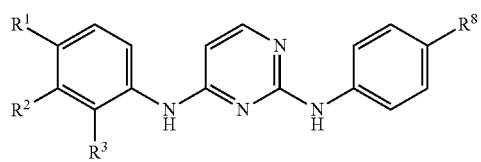

wherein $R^1$, $R^2$, $R^3$ and $R^8$ are as defined in Table 8, may be prepared by following the procedure of Example 1 but using the appropriate starting materials.

TABLE 8

| Ex | $R^1$ | $R^2$ | $R^3$ | $R^8$ | *ES+ | *ES- |
|---|---|---|---|---|---|---|
| 169 | 4-morpholino | —H | —H | —H | | |
| 170 | —CH═N—NH— | | —H | —H | 363 | 361 |
| 171 | —OCH$_3$ | —OH | —H | —H | 446 | |
| 172 | —CH$_3$ | —H | —SO$_2$NH$_2$ | —OCH$_3$ | 446 | |

The compounds of formula X$_9$

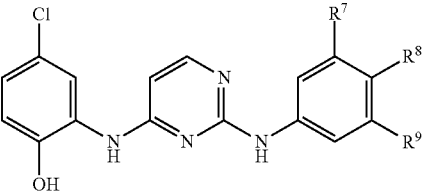

wherein $R^7$, $R^8$ and $R^9$ are as defined in Table 9, may be prepared by following the procedure of Example 1 but using the appropriate starting materials.

TABLE 9

| Example | $R^7$ | $R^8$ | $R^9$ | *ES+ | *ES- |
|---|---|---|---|---|---|
| 173 | —O—CH$_2$CH$_2$-1-piperidyl | —OCH$_3$ | —H | 470.3 | 468.3 |
| 174 | —O-(1-methyl-azacyclohept-4-yl) | —H | —H | 440 | |
| 175 | —O-(1-methyl-azacyclopent-2-yl) | —H | —H | 440 | 438 |

TABLE 9-continued

| Example | R⁷ | R⁸ | R⁹ | *ES+ | *ES− |
|---|---|---|---|---|---|
| 176 | —O—CH₂CH₂—CH₂-1-imidazolyl | —OCH₃ | —H | 467 | 465 |
| 177 | —OCH₃ | —OCH₃ | —OCH₃ | | |
| 178 | —O—CH₂CH₂-1-(1,2,4-triazolyl) | —H | —H | 424 | 422 |
| 179 | —O—CH₂CH₂-1-piperidyl | —H | —H | | |
| 180 | —O—CH₂CH₂—OH | —OCH₃ | —H | | |
| 181 | —O—CH₂CH₂-4-morpholino | —H | —H | 442 | 440 |
| 182 | —O—CH₂CH₂CH₂-1-imidazolyl | —H | —H | | |

TABLE 10

| EX | R¹ | R⁷ | R⁹ | *ES+ | *ES− |
|---|---|---|---|---|---|
| 183 | —CH₂CH₂—OH | —OCH₃ | —OCH₃ | 411 | 409 |
| 184 | —SO₂NH₂ | —O—CH₂CH₂-1-imidazolyl | —H | 496.3 | 494.3 |

The compounds of formula X₁₁

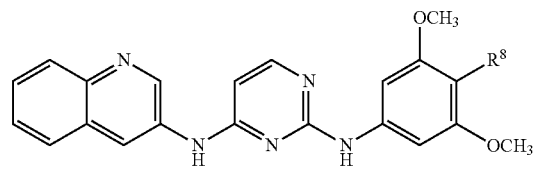

wherein R⁸ is —OCH₃ (Example 185) or —OH (Example 186), may be prepared by following the procedure of Example 1 but using the appropriate starting materials.

The compounds of formula X₁₀

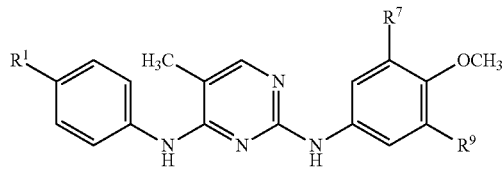

wherein R¹, R⁷ and R⁹ are as defined in Table 10, may be prepared by following the procedure of Example 1 but using the appropriate starting materials.

The compounds of formula X₁₂

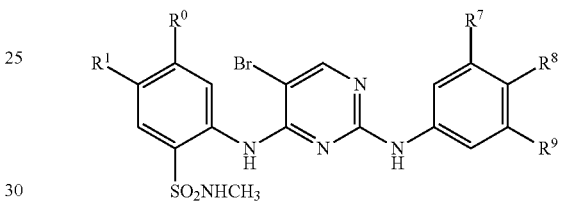

wherein R⁰, R¹, R⁷, R⁸ and R⁹ are as defined in Table 12, may be prepared by following the procedure of Example 1 but using the appropriate starting materials.

TABLE 12

| Example | R⁰ | R¹ | R⁷ | R⁸ | R⁹ |
|---|---|---|---|---|---|
| 187 | —H | —H | —H | —SO₂NH₂ | —H |
| 188 | —H | —H | —H | —H | —CH₃ |
| 189 | —H | —H | —H | —CH₃ | —H |
| 190 | —H | —F | —OCH₃ | —OCH₃ | —OCH₃ |
| 191 | —H | —H | —H | —CH₃ | —CH₃ |
| 192 | —H | —H | —CH₃ | —H | —CH₃ |
| 193 | —H | —H | —OCH₃ | —CH₃ | —H |
| 194 | —H | —H | —H | —H | —N(CH₃)₂ |
| 195 | —H | —H | —OCH(CH₃)₂ | —H | —H |
| 196 | —H | —H | —H | —OCH(CH₃)₂ | —H |
| 197 | —H | —H | —CH(CH₃)₂ | —H | —H |
| 198 | —H | —H | —H | —CH=N—NH— | |
| 199 | —H | —H | —OCH₃ | —CH₃ | —OCH₃ |
| 200 | —OCH₃ | —H | —OCH₃ | —OCH₃ | —OCH₃ |
| 201 | —H | —H | —H | —H | —H |
| 202 | —CH₃ | —Cl | —OCH₃ | —OCH₃ | —OCH₃ |
| 203 | —H | —H | —H | —H | —CF₃ |
| 204 | —Cl | —CH₃ | —OCH₃ | —OCH₃ | —OCH₃ |
| 205 | —H | —H | —H | —NH—CH=N— | |
| 206 | —H | —H | —H | —N(—CH₂CH₂CH₂-4-morpholino)-CH=CH— | |
| 207 | —H | —H | —H | —CH₂CH₂—CH₂— | —H |

The compounds of formula $X_{13}$

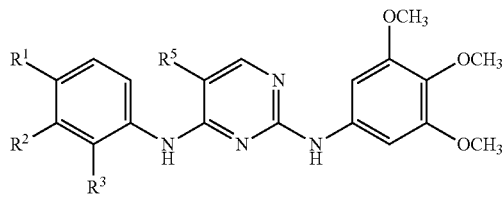

wherein $R^1$, $R^2$, $R^3$ and $R^5$ are as defined in Table 13, may be prepared by following the procedure of Example 1 but using the appropriate starting materials.

TABLE 13

| Example | $R^1$ | $R^2$ | $R^3$ | $R^5$ | *ES+ | *ES− |
|---|---|---|---|---|---|---|
| 208 | —H | —H | —SO$_2$NHCH$_3$ | —CF$_3$ | 514.0 | |
| 209 | —H | —H | —SO$_2$NHC$_3$H$_7$ | —Br | | |
| 210 | —H | —H | —SO$_2$NH—CH$_2$CH-cyclopropyl | —Br | | |
| 211 | —H | —H | —SO$_2$NHCH$_3$ | —CH$_3$ | | |
| 212 | —H | —H | —SO$_2$N(CH$_3$)$_2$ | —Br | | |
| 213 | —H | —H | —SO$_2$NHCH$_3$ | —Cl | | |
| 214 | —H | —H | —SO$_2$NHCH$_3$ | —I | | |
| 215 | —H | —H | —SO$_2$NHCH$_3$ | —Br | | |
| 216 | —CH$_3$ | —OCH$_3$ | —SO$_2$NH$_2$ | —H | 476 | 474 |
| 217 | —H | piperidino | —SO$_2$NH$_2$ | —H | 515.5 | 513.4 |
| 218 | —H | morpholino | —SO$_2$NH$_2$ | —H | 517.4 | 515.4 |
| 219 | —H | —C$_2$H$_5$ | —SO$_2$NH$_2$ | —H | | |
| 220 | —H | —CH$_3$ | —SO$_2$NH$_2$ | —Cl | | |
| 221 | —H | —CH$_3$ | —SO$_2$NHCH$_3$ | —H | 460.4 | |
| 222 | —H | phenyl | —SO$_2$NH$_2$ | —H | 508.2 | 506.3 |

The compounds of formula $X_{14}$

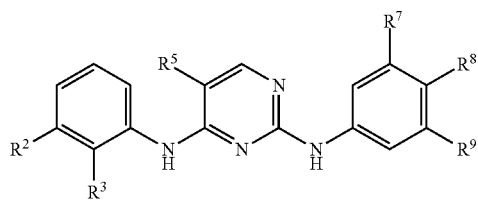

wherein $R^2$, $R^3$, $R^5$, $R^7$, $R^8$ and $R^9$ are as defined in Table 14, may be prepared by following the procedure of Example 1 but using the appropriate starting materials.

TABLE 14

| Ex | $R^2$ | $R^3$ | $R^5$ | $R^7$ | $R^8$ | $R^9$ | *ES+ | *ES− |
|---|---|---|---|---|---|---|---|---|
| 223 | —OCH$_3$ | —SO$_2$NH$_2$ | —H | —H | —CH=N—N(CH$_3$)— | | | 424 |
| 224 | —OCH$_3$ | —SO$_2$NH$_2$ | —H | —O—CH$_2$CH$_2$—OCH$_3$ | —OCH$_3$ | —H | 476.2 | 474.3 |
| 225 | —OCH(CH$_3$)$_2$ | —SO$_2$NH$_2$ | —H | —O—CH$_2$CH$_2$-piperidino | —OCH$_3$ | —H | 551.2 | 555.3 |
| 226 | —OCH$_3$ | —SO$_2$NH$_2$ | —H | —O—CH$_2$CH$_2$-(4-methyl-piperazin-1-yl) | —H | —H | 514.3 | 512.3 |
| 227 | —OCH$_3$ | —SO$_2$NH$_2$ | —H | -morpholino | —OCH$_3$ | —H | 487.1 | 485.2 |
| 228 | —CH$_3$ | —SO$_2$NH$_2$ | —H | —O—CH$_2$CH$_2$-piperidino | —OCH$_3$ | —H | 527.3 | |
| 229 | —CH$_3$ | —SO$_2$NH$_2$ | —H | —O—CH$_2$CH$_2$CH$_2$-1-pyrrolidinyl | —OCH$_3$ | —H | 513.2 | 511.3 |
| 230 | —O—CH$_2$CH$_2$—OCH$_3$ | —SO$_2$NH$_2$ | —H | —H | —CH=N—N(CH$_3$)— | | 539 | 537 |
| 231 | -(4-methyl-piperazin-1-yl) | —SO$_2$NH$_2$ | —H | —OCH$_3$ | —OCH$_3$ | —OCH$_3$ | 530.4 | 528.4 |

TABLE 14-continued

| Ex | $R^2$ | $R^3$ | $R^5$ | $R^7$ | $R^8$ | $R^9$ | *ES+ | *ES− |
|---|---|---|---|---|---|---|---|---|
| 232 | —OCH$_3$ | —SO$_2$NH$_2$ | —H | —O—CH$_2$CH$_2$—OH | —OCH$_3$ | —H | 462.2 | 460.3 |
| 233 | —OCH$_3$ | —SO$_2$NH$_2$ | —Br | —O—CH$_2$CH$_2$—OCH$_3$ | —OCH$_3$ | —H | | |
| 234 | —CH$_3$ | —SO$_2$NH$_2$ | —H | —O—CH$_2$CH$_2$-(4-methyl-piperazin-1-yl) | —OCH$_3$ | —H | 528.2 | 526.3 |
| 235 | —CH$_3$ | —SO$_2$NH$_2$ | —H | —O—CH$_2$CH$_2$—N(CH$_3$)$_2$ | —H | —H | 443.2 | 441.3 |
| 236 | —H | —SO$_2$NH$_2$ | —H | —O—CH$_2$CH$_2$-1-pyrrolidinyl | —OCH$_3$ | —H | 485.2 | 483.3 |
| 237 | —CH$_3$ | —SO$_2$NH$_2$ | —H | —H | —N(CH$_3$)—N=CH— | | 410 | |
| 238 | —CH$_3$ | —SO$_2$NH$_2$ | —H | —CH$_3$ | —OCH$_3$ | OCH$_3$ | | |
| 239 | —CH$_3$ | —SO$_2$NH$_2$ | —Br | —O—CH$_2$CH$_2$—OCH$_3$ | —OCH$_3$ | —H | 538/540 | |
| 240 | —OCH$_3$ | —SO$_2$NH$_2$ | —H | —OCH$_3$ | —H | —H | 402.2 | 400.2 |
| 241 | —H | —SO$_2$NH$_2$ | —H | —H | —CO—NH—CH$_2$CH$_2$—OCH$_3$ | —H | | |

ES+ means electrospray MS positive mode; ES− means electrospray MS negative mode; and EL means electron impact MS.

The compounds of formula I and their pharmaceutically acceptable salts, exhibit valuable pharmacological properties when tested in in vitro assays, and are therefore useful as pharmaceuticals.

In particular the compounds of the invention exhibit ZAP-70 (zeta chain-associated protein of 70 kD), Focal Adhesion Kinase (FAK) and/or Syk protein tyrosine kinases inhibiting activity. More particularly the compounds of the invention are active at the human ZAP-70, FAK and/or Syk protein tyrosine kinases. ZAP-70, FAK and/or Syk protein tyrosine kinase interaction of the compounds of the invention may be demonstrated by their ability to prevent phosphorylation of e.g. LAT-11 (SEQ ID NO: 1) by human ZAP-70 protein tyrosine kinase, to prevent phosphorylation of e.g. Biot-Y397 (SEQ ID NO:2) by human FAK protein tyrosine kinase, and/or to prevent phosphorylation of e.g. polymeric glutamic acid-tyrosine (Glu, Tyr) by human Syk protein tyrosine kinase in, e.g. aqueous solution, e.g. as demonstrated in accordance with the following test methods.

1. Cell-Free Kinase Assays: ZAP-70 and Syk Kinase Assays

ZAP-70, Lck and Syk are commercially available from Upstate Biotechnology, Lake Placid, N.Y.

Preparation of LAT-11 (SEQ ID NO:1): The peptide LAT-11 used as a substrate in the ZAP-70 kinase assay may be prepared as disclosed in Example 1A of WO 02/12275, the contents of which, particularly with reference to Example 1A, is incorporated herein by reference.

ZAP-70 Kinase assay: The activities of the agents of invention are determined in a homogenous ZAP-70 kinase assay based on time-resolved fluorescence resonance energy transfer. Briefly, 80 nM ZAP-70 are incubated with 80 nM Lck and 4 μM ATP in ZAP-70 kinase buffer (20 mM Tris, pH 7.5, 10 μM Na$_3$VO$_4$, 1 mM DTT, 1 mM MnCl$_2$, 0.01% bovine serum albumin, 0.05% Tween 20) for 1 hour at room temperature in a siliconized polypropylene tube. Then, the selective Lck inhibitor PP2 (4-amino-5-(4-chloro-phenyl)-7-(t-butyl)pyrazolo[3,4-d]pyrimidine; Alexis Biochemicals) is added (final concentration 1.2 μM) and incubated for further 10 min. Ten μl of this solution is mixed with the 10 μl biotinylated peptide LAT-11 (1 μM) as substrate and 20 μl of serial dilutions of inhibitors and incubated for 4 hours at room temperature. The kinase reaction is terminated with 10 μl of a 10 mM EDTA solution in detection buffer (20 mM Tris, pH 7.5, 0.01% bovine serum albumin, 0.05% Tween 20). The detection phase is performed by addition of 50 μl europium (Eu)-labelled anti-phosphotyrosine antibody (e.g. Eu-PT66; final concentration 0.125 nM; Advant/Wallac) and 50 μl streptavidin-allophycocyanine (SA-APC; final concentration 40 nM) in detection buffer. After 1 hour incubation at room temperature fluorescence is measured, e.g., on the Victor2 Multilabel Counter (Wallac) at 665 nm. Background values (low control) are obtained in the absence of test samples and ATP and are subtracted from all values. Signals obtained in the absence of test samples are taken as 100% (high control). The inhibition obtained in the presence of test compounds was calculated as percent inhibition of the high control. The concentration of test compounds resulting in 50% inhibition (IC$_{50}$) was determined from the dose-response curves. In this assay, the compounds of the invention have IC$_{50}$ values in the range of 10 nM to 2 μM, preferably from 10 nM to 100 nM. Compound of Example 4 shows an IC$_{50}$ value of 12 nM.

Syk Kinase assay: The activities of the agents of invention are determined in a heterogenous Syk kinase assay based on the dissociation-enhanced lanthanide fluoroimmunoassay (DELFIA) technology. This method utilizes europium chelate-labelled anti-phosphotyrosine antibodies to detect phosphate transfer by Syk to a polymeric glutamic acid-tyrosine (Glu, Tyr) substrate coated onto microtiter plates as described (Braunwalder A F, Yarwood D R, Sills M A, Lipson K E. Measurement of the protein tyrosine kinase activity of c-src using time-resolved fluorometry of europium chelates. Anal. Biochem. 1996; 238(2):159-64). The amount of phosphorylation is then quantified with time-resolved, dissociation-enhanced fluorescence. Briefly, hundred μl of poly (Glu, Tyr) (4:1; 2 μg/ml in phosphate-buffered saline, PBS) are coated to ELISA plates overnight at room temperature. The poly (Glu, Tyr) solution is removed and 250 μl of 1% bovine serum albumin in PBS are added for one hour at room temperature. Plates are then washed three times with 350 μl of washing buffer (25 mM Tris-HCl, pH 7.4 containing 0.03% Tween-20). The kinase reaction is performed for one hour at room temperature by mixing serial dilutions of inhibitors in 30 μl with 30 μl of Syk kinase (20 ng/ml) and ATP (1 μM) in kinase buffer (20 mM Tris, pH 7.5, 10 μM Na$_3$VO$_4$, 1 mM DTT, 10 mM MnCl$_2$, 2 mM MgCl$_2$, 0.01% bovine serum albumin, 0.05% Tween 20). After washing the plates four times as described above 60 μl DELFIA europium N1-labelled anti-phosphotyrosine antibody PY20 (Advant/Wallac) are added (100 ng/ml in 50 mM Tris-HCl, pH7.4, 150 mM NaCl, 20 μM Titriplex V, 0.2% bovine serum albumine, 0.05% Tween-20) and incubated for one hour at room temperature. Plates are washed eight times and 60 μl enhancement solution (Wallac) are added. Fluorescence is determined at 615 nm (Victor2; Wallac). High control values (100% signal) are obtained in absence of test samples and low control values (background) in absence of test samples and ATP. Low controls were subtracted from all values. The inhibition obtained in the presence of test compounds was calculated as percent inhibition of the high control. The concentration of test compounds resulting in 50% inhibition (IC$_{50}$) was determined from the dose-response curves. In this assay, the compounds of the invention have $IC_{50}$ values in the range of 100 nM to 10 μM, preferably from 100 to 1 μM. Compound of Example 128 has an $IC_{50}$ value of 150 nM.

2. Allogeneic Mixed Lymphocyte Reaction (MLR)

Compounds of the invention exhibit T cell inhibiting activity. More particular the compounds of the invention prevent T cell activation and/or proliferation in e.g. aqueous solution, e.g. as demonstrated in accordance with the following test method. The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice ($1.6 \times 10^5$ cells from each strain per well in flat bottom tissue culture microtiter plates, $3.2 \times 10^5$ in total) are incubated in RPMI medium containing 10% FCS, 100 U/ml penicillin, 100 μg/ml streptomycin (Gibco BRL, Basel, Switzerland), 50 μM 2-mercaptoethanol (Fluka, Buchs, Switzerland) and serially diluted compounds. Seven three-fold dilution steps in duplicates per test compound are performed. After four days of incubation 1 μCi $^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined. In this assay, the compounds of the invention have $IC_{50}$ values in the range of 10 nM to 10 μM, preferably from 10 nM to 100 nM. Compound of Example 120 shows an $IC_{50}$ value of 13 nM.

3. FAK Assay

All steps are performed in a 96-well black microtiter plate. Purified recombinant hexahistidine-tagged human FAK kinase domain is diluted with dilution buffer (50 mM HEPES, pH 7.5, 0.01% BSA, 0.05% Tween-20 in water) to a concentration of 94 ng/mL (2.5 nM). The reaction mixture is prepared by mixing 10 μL 5× kinase buffer (250 mM HEPES, pH 7.5, 50 μM Na$_3$VO$_4$, 5 mM DTT, 10 mM MgCl$_2$, 50 μM MnCl$_2$, 0.05% BSA, 0.25% Tween-20 in water), 20 μL water, 5 μL of 4 μM biotinylated peptide substrate (Biot-Y397) in aqueous solution, 5 μL of test compound in DMSO, and 5 μL of recombinant enzyme solution and incubated for 30 min at room temperature. The enzyme reaction is started by addition of 5 μL of 5 μM ATP in water and the mixture is incubated for 3 hours at 37° C. The reaction is terminated by addition of 200 μL of detection mixture (1 nM Eu-PT66, 2.5 μg/mL SA-(SL) APC, 6.25 mM EDTA in dilution buffer), and the FRET signal from europium to allophycocyanin is measured by ARVOsx+L (Perkin Elmer) after 30 min of incubation at room temperature. The ratio of fluorescence intensity of 665 nm to 615 nm is used as a FRET signal for data analysis in order to cancel the colour quenching effect by a test compound. The results are determined as percent inhibition of enzyme activity. DMSO and 0.5 M EDTA are used as a control of 0% and 100% inhibition, respectively. $IC_{50}$ values are determined by non-linear curve fit analysis using the OriginPro 6.1 program (OriginLab). In this assay the compounds of formula I inhibit FAK activity at a $IC_{50} < 1$ μM. Examples 188, 208 and 213 show $IC_{50}$ values of 15 nM, 1 nM and 7 nM respectively.

The Biot-Y397 peptide (Biotin-SETDDYAEIID ammonium salt, SEQ ID NO:2) is designed to have the same amino acid sequence as the region from S392 to D402 of human (GenBank Accession Number L13616) and is prepared by standard methods.

Purified recombinant hexahistidine-tagged human FAK kinase domain is obtained in the following way: Full-length human FAK cDNA is isolated by PCR amplification from human placenta Marathon-Ready™ cDNA (Clontech, No. 7411-1) with the 5' PCR primer (ATGGCAGCTGCTTAC-CTTGAC, SEQ ID NO:3) and the 3' PCR primer (TCAGT-GTGGTCTCGTCTGCCC, SEQ ID NO:4) and subcloned into a pGEM-T vector (Promega, No. A3600). After digestion with AccIII, the purified DNA fragment is treated with Klenow fragment. The cDNA fragment is digested with BamHI and cloned into pFastBacHTb plasmid (Invitrogen Japan K.K., Tokyo) previously cut with BamHI and Stu I. The resultant plasmid, hFAK KD (M384-G706)/pFastBacHTb, is sequenced to confirm its structure. The resulting DNA encodes a 364 amino acid protein containing a hexahistidine tag, a spacer region and a rTEV protease cleavage site at the N-terminal and the kinase domain of FAK (Met384-Gly706) from position 29 to 351.

Donor plasmid is transposed into the baculovirus genome, using MaxEfficacy DH10Bac E. coli cells. Bacmid DNA is prepared by a simple alkaline lysis protocol described in the Bac-to-Bac® Baculovirus Expression system (Invitrogen). Sf9 insect cells are transfected based on the protocol provided by the vendor (CellFECTIN®, Invitrogen). The expression of FAK in each lysate is analysed by SDS-PAGE and Western blotting with anti-human FAK monoclonal antibody (clone #77 from Transduction Laboratories).

The virus clone that shows the highest expression is further amplified by infection to Sf9 cells. Expression in ExpresSF+® cells (Protein Sciences Corp., Meriden, Conn., USA) gives high level of protein with little degradation. Cell lysates are loaded onto a column of HiTrap™ Chelating Sepharose HP (Amersham Biosciences) charged with nickel sulfate and equilibrated with 50 mM HEPES pH 7.5, 0.5 M NaCl and 10 mM imidazole. Captured protein is eluted with increasing amounts of imidazole in HEPES buffer/NaCl, and further purified by dialysis in 50 mM HEPES pH 7.5, 10% glycerol and 1 mM DTT.

4. Phosphorylation Levels of FAK

Phosphorylation levels of FAK at Tyr397 are quantified by the sandwich ELISA. Mouse mammary carcinoma 4T1 cells ($1 \times 10^5$) are plated in wells of 96-well culture plates and incubated with or without various concentrations of a compound of formula I for 1 h in Dulbecco's modified eagle medium containing 10% FBS. The medium is removed and cells are lysed in 200 μL 50 mM Tris-HCl, pH 7.4, containing 1% NP-40, 0.25% sodium deoxycholate, 150 mM NaCl, 1 mM EDTA, 1 mM PMSF, 1 mM Na$_3$VO$_4$, 1 mM NaF, 1 μg/mL aprotinin, 1 μg/mL leupeptin and 1 μg/mL pepstatin. After centrifugation, the supernatants are subjected to a sandwich ELISA to quantify the phosphorylated FAK and total FAK. Cell lysates are applied to 96-well flat-bottom ELISA plates which have been pre-coated with 100 μL/well of 4 μg/mL mouse monoclonal anti-FAK antibody (clone 77, Becton Dickinson Transduction Laboratories) in 50 mM Tris-HCl, pH 9.5, containing 150 mM NaCl for 18 h at 4° C. and blocked with 300 μL of BlockAce (Dainippon Pharmaceuticals Co.) diluted at 1:4 with H$_2$O at room temperature for 2 h. After washing with TBSN (20 mM Tris-HCl, pH 8.3, containing 300 mM NaCl, 0.1% SDS and 0.05% NP-40), total FAK is detected with 100 μL of 1 μg/ml anti-FAK polyclonal antibody (#65-6140, Upstate Biology Inc.), and phosphorylated FAK is detected with 100 μL of 0.25 μg/4 anti-phosphorylated FAK (Y397) antibody (Affinity BioReagents,

OPA1-03071) in BlockAce diluted at 1:10 with $H_2O$. After 1 h incubation at room temperature, plates are washed with TBSN and 100 µL of biotinylated anti-rabbit IgG (#65-6140, Zymed Laboratories Inc.) diluted at 1:2000 with BlockAce diluted at 1:10 with $H_2O$ is incubated at room temperature for 1 h. After washing with TBSN, ABTS solution substrate kit (#00-2011, Zymed Laboratories Inc.) is used for color development. Absorbance at 405 nm is measured after 20 min incubation at room temperature. The concentration of compound causing 50% reduction of phosphorylation level of FAK ($IC_{50}$) is determined. In this assay, compounds of formula I reduce phosphorylation at an $IC_{50}$ of <1 µM. Examples 190, 198 and 210 show $IC_{50}$ values of 0.44 µM, 0.043 µM and 0.01 µM respectively.

5. Anchorage-Independent Tumor Cell Growth Assay

Mouse mammary carcinoma 4T1 cells ($5×10^3$) are plated in 96-well Ultra low Attachment plates (#3474, Corning Inc.) in 100 4 of Dulbecco's modified eagle medium containing 10% FBS. Cells are cultured for 2 h and inhibitors are added at various concentrations in a final concentration of 0.1% DMSO. After 48 h, cell growth is assayed with the cell counting kit-8 (Wako Pure Chemical), which uses a water soluble tetrazolium salt WST8. Twenty µL of the reagent is added into each well and cells are further cultured for 2 h. The optical density is measured at 450 nm. The concentration of compound causing 50% inhibition of growth may thus be determined. Examples 204, 213 and 206 show $IC_{50}$ values of 0.4 µM, 0.016 µM and 0.09 µM respectively.

The compounds of the invention are therefore useful in the prevention or treatment of disorders or diseases where ZAP-70 inhibition, and/or Syk inhibition play a role, e.g. diseases or disorders mediated by T lymphocytes, B lymphocytes, mast cells and/or eosinophils e.g. acute or chronic rejection of organ or tissue allo- or xenografts, atheriosclerosis, vascular occlusion due to vacular injury such as angioplasty, restenosis, hypertension, heart failure, chronic obstructive pulmonary disease, CNS disease such as Alzheimer disease or amyotrophic lateral sclerosis, cancer, infectious disease such as AIDS, septic shock or adult respiratory distress syndrome, ischemia/reperfusion injury e.g. myocardial infarction, stroke, gut ischemia, renal failure or hemorrhage shock, or traumatic shock. The agent of the invention are also useful in the treatment and/or prevention of acute or chronic inflammatory diseases or disorders or autoimmune diseases e.g. rheumatoid arthritis, osteoarthritis, systemic lupus erythematosus, Hashimoto's thyroidis, multiple sclerosis, myasthenia gravis, diabetes (type I and II) and the disorders associated with therewith, respiratory diseases such as asthma or inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis.

Compounds of the invention are also useful in the prevention or treatment of conditions caused by a malfunction of signal cascades connected with FAK, e.g. tumors, for example brain and other central nervous system tumors (eg. tumors of the meninges, brain, spinal cord, cranial nerves and other parts of central nervous system, e.g. glioblastomas or medulla blastomas); head and/or neck cancer; breast tumors; circulatory system tumors (e.g. heart, mediastinum and pleura, and other intrathoracic organs, vascular tumors and tumor-associated vascular tissue); excretory system tumors (e.g. kidney, renal pelvis, ureter, bladder, other and unspecified urinary organs); gastrointestinal tract tumors (e.g. oesophagus, stomach, small intestine, colon, colorectal, rectosigmoid junction, rectum, anus and anal canal), tumors involving the liver and intrahepatic bile ducts, gall bladder, other and unspecified parts of biliary tract, pancreas, other and digestive organs); head and neck; oral cavity (lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx); reproductive system tumors (e.g. vulva, vagina, Cervix uteri, Corpus uteri, uterus, ovary, and other sites associated with female genital organs, placenta, penis, prostate, testis, and other sites associated with male genital organs); respiratory tract tumors (e.g. nasal cavity and middle ear, accessory sinuses, larynx, trachea, bronchus and lung, e.g. small cell lung cancer or non-small cell lung cancer); skeletal system tumors (e.g. bone and articular cartilage of limbs, bone articular cartilage and other sites); skin tumors (e.g. malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites, tumors of blood and lymphatic system (e.g. Hodgkin's disease, Non-Hodgkin's lymphoma, Burkitt's lymphoma, AIDS-related lymphomas, malignant immunoproliferative diseases, multiple myeloma and malignant plasma cell neoplasms, lymphoid leukemia, acute or chronic myeloid leukemia, acute or chronic lymphocytic leukemia, monocytic leukemia, other leukemias of specified cell type, leukemia of unspecified cell type, other and unspecified malignant neoplasms of lymphoid, haematopoietic and related tissues, for example diffuse large cell lymphoma, T-cell lymphoma or cutaneous T-cell lymphoma). Myeloid cancer includes e.g. acute or chronic myeloid leukaemia.

Where hereinbefore and subsequently a tumor, a tumor disease, a carcinoma or a cancer is mentioned, also metastasis in the original organ or tissue and/or in any other location are implied alternatively or in addition, whatever the location of the tumor and/or metastasis is.

The compositions of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Pharmaceutical compositions comprising an agent of the invention in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance. Topical administration is e.g. to the skin. A further form of topical administration is to the eye.

The compounds of formula I may be administered in free form or in pharmaceutically acceptable salt form, e.g. as indicated above. Such salts may be prepared in conventional manner and exhibit the same order of activity as the free compounds.

In accordance with the foregoing, the present invention also provides:

(1) A compound of formula I or a pharmaceutically acceptable salt thereof, for use as a pharmaceutical;
(2) A compound of formula I or a pharmaceutically acceptable salt thereof, for use as a ZAP-70, FAK and/or Syk tyrosine kinase inhibitor, for example for use in any of the particular indications hereinbefore set forth;
(3) A pharmaceutical composition, e.g. for use in any of the indications herein before set forth, comprising a compound of formula I or a pharmaceutically acceptable salt thereof, together with one or more pharmaceutically acceptable diluents or carriers therefor.
(4) A method for the treatment of any of particular indication hereinbefore set forth in a subject in need thereof which comprises administering an effective amount of a compound of formula I or a pharmaceutically acceptable salt thereof;
(5) The use of a compound of formula I or a pharmaceutically acceptable salt thereof, for the manufacture of a medicament for the treatment or prevention of a disease or condition in which ZAP-70, FAK and/or Syk tyrosine kinase activation plays a role or is implicated; e.g. as discussed above.

Compounds of the invention may be administered as the sole active ingredient or together with other drugs useful against neoplastic diseases, inflammatory disorders or in immunomodulating regimens. For example, the compounds of the invention may be used in combination with an active agent effective in various diseases as described above, e.g. with cyclosporins, rapamycins or ascomycins, or their immunosuppressive analogs or derivatives, e.g. cyclosporin A, cyclosporin G, Isa tx247, FK-506, sirolimus or everolimus; CCI-779, ABT578, AP23573, corticosteroids e.g. prednisone; cyclophosphamide; azathioprene; methotrexate; gold salts, sulfasalazine, antimalarials; leflunomide; mizoribine; mycophenolic acid; mycophenolate mofetil; 15-deoxyspergualine; an EDG receptor agonist having accelerating lymphocyte homing activity, e.g FTY720 or an analogue thereof, immuno-suppressive monoclonal antibodies, e.g. monoclonal antibodies to leukocyte receptors, e.g. MHC, CD2, CD3, CD4, CD7, CD25, CD28, CD40, CD45, CD58, CD80, CD86, CD152, CD137, CD154, ICOS, LFA-1, VLA-4 or their ligands; or other immunomodulatory compounds, e.g. CTLA4Ig.

A compound of formula I may also be used to advantage in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide (TEMODAL®).

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. A combination of the invention comprising an antineoplastic agent which is an aromatase inhibitor may particularly be useful for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride.

The term "topoisomerase I inhibitors" as used herein includes, but is not limited to topotecan, irinotecan, 9-nitrocamptothecin and the macromolecular camptothecin conjugate PNU-166148 (compound A1 in WO99/17804).

The term "topoisomerase II inhibitors" as used herein includes, but is not limited to the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide.

The term "microtubule active agents" relates to microtubule stabilizing and microtubule destabilizing agents including, but not limited to the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D.

The term "alkylating agents" as used herein includes, but is not limited to cyclophosphamide, ifosfamide and melphalan.

The term "histone deacetylase inhibitors" relates to compounds which inhibit the histone deacetylase and which possess antiproliferative activity.

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enzyme (COX-2) and which possess antiproliferative activity such as celecoxib (Celebrex®), rofecoxib (Vioxx®) and lumiracoxib (COX189).

The term "MMP inhibitors" relates to compounds which inhibit the matrix metalloproteinase (MMP) and which possess antiproliferative activity.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cis-platin and oxaliplatin.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, Platelet-derived Growth Factor (PDGF), Bcr-Abl tyrosine kinase, c-kit, Flt-3 and Insulin-like Growth Factor I Receptor (IGF-IR) and Cyclin-dependent kinases (CDKs), and anti-angiogenic compounds having another mechanism of action than decreasing the protein kinase activity.

Compounds which decrease the activity of VEGF are especially compounds which inhibit the VEGF receptor, especially the tyrosine kinase activity of the VEGF receptor, and compounds binding to VEGF, and are in particular those compounds, proteins and monoclonal antibodies generically and specifically disclosed in WO 98/35958 (describing compounds of formula I), WO 00/09495, WO 00/27820, WO 00/59509, WO 98/11223, WO 00/27819, WO 01/55114, WO 01/58899 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, vol. 27, no. 1, pp 14-21, 1999; in WO 00/37502 and WO 94/10202; Angiostatin™, described by M. S. O'Reilly et al, Cell 79, 1994, 315-328; and Endostatin™ described by M. S. O'Reilly et al, Cell 88, 1997, 277-285;

compounds which decrease the activity of EGF are especially compounds which inhibit the EGF receptor, especially the tyrosine kinase activity of the EGF receptor, and compounds binding to EGF, and are in particular those compounds generically and specifically disclosed in WO 97/02266 (describing compounds of formula IV), EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980;

compounds which decrease the activity of c-Src include, but are not limited to, compounds inhibiting the c-Src protein tyrosine kinase activity as defined below and to SH2 interaction inhibitors such as those disclosed in WO97/07131 and WO97/08193;

compounds inhibiting the c-Src protein tyrosine kinase activity include, but are not limited to, compounds belonging to the structure classes of pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrido[2,3-d]pyrimidines. Preferably, the term relates to those compounds disclosed in WO 96/10028, WO 97/28161, WO97/32879 and WO97/49706;

compounds which decreases the activity of the protein kinase C are especially those staurosporine derivatives disclosed in EP 0 296 110 (pharmaceutical preparation described in WO 00/48571) which compounds are protein kinase C inhibitors;

further specific compounds that decrease protein kinase activity and which may also be used in combination with the compounds of the present invention are Imatinib (Gleevec®/Glivec®), PKC412, Iressa™ (ZD1839), PK1166, PTK787, ZD6474, GW2016, CHIR-200131, CEP-7055/CEP-5214, CP-547632 and KRN-633;

anti-angiogenic compounds having another mechanism of action than decreasing the protein kinase activity include, but are not limited to e.g. thalidomide (THALOMID), celecoxib (Celebrex), SU5416 and ZD6126.

The term "gonadorelin agonist" as used herein includes, but is not limited to abarelix, goserelin and goserelin acetate. Goserelin is disclosed in U.S. Pat. No. 4,100,274.

The term "anti-androgens" as used herein includes, but is not limited to bicalutamide (CASODEX™), which can be formulated, e.g. as disclosed in U.S. Pat. No. 4,636,505.

The term "bengamides" relates to bengamides and derivatives thereof having antiproliferative properties.

The term "bisphosphonates" as used herein includes, but is not limited to etridonic acid, clodronic acid, tiludronic acid, pamidronic acid, alendronic acid, ibandronic acid, risedronic acid and zoledronic acid.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan®), PRO64553 (anti-CD40) and 2C4 Antibody.

The structure of the active agents identified by code nos., generic or trade names may be taken from the actual edition of the standard compendium "The Merck Index" or from databases, e.g. Patents International (e.g. IMS World Publications).

In accordance with the foregoing the present invention provides in a yet further aspect:

(6) A method as defined above comprising co-administration, e.g. concomitantly or in sequence, of a therapeutically effective amount of a) a compound of formula I or a pharmaceutically acceptable salt thereof, and b) a second drug substance, said second drug substance being for example for use in any of the particular indications hereinbefore set forth.

(7) A combination comprising a therapeutically effective amount of a ZAP-70, FAK and/or Syk tyrosine kinase inhibitor, e.g. a compound of formula I or a pharmaceutically acceptable salt thereof, and a second drug substance, said second drug substance being for example as disclosed above.

Where a ZAP-70, FAK and/or Syk tyrosine kinase inhibitor, e.g. a compound of formula I, is administered in conjunction with other immunosuppressive/immunomodulatory, anti-inflammatory or antineoplastic agent, e.g. as disclosed above, dosages of the co-administered drug or agent will of course vary depending on the type of co-drug or -agent employed, or the specific drug or agent used, or the condition being treated and so forth.

Representative FAK inhibitors are the compounds of Examples Nos. 187-203 and 209-212.

The invention claimed is:

1. A compound of formula I

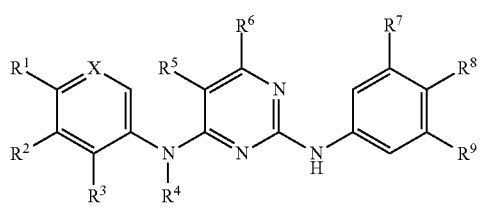

(I)

wherein
X is =$CR^0$—;
$R^0$ is hydrogen;
$R^2$ is —$SO_2N(R^{10})R^{11}$;
each of $R^1$ and $R^3$ independently is hydrogen; hydroxy; $C_1$-$C_8$alkyl; $C_2$-$C_8$alkenyl; $C_3$-$C_8$cycloalkyl; $C_3$-$C_8$cycloalkyl-$C_1$-$C_8$alkyl; hydroxy$C_1$-$C_8$alkyl; $C_1$-$C_8$alkoxy$C_1$-$C_8$alkyl; hydroxy$C_1$-$C_8$alkoxy$C_1$-$C_8$alkyl; aryl$C_1$-$C_8$alkyl which optionally may be substituted on the ring by hydroxy, $C_1$-$C_8$alkoxy, carboxy or $C_1$-$C_8$alkoxycarbonyl;
or each of $R^1$ and and $R^3$, independently, is halogen; halo-$C_1$-$C_8$alkyl; $C_1$-$C_8$alkoxy; halo-$C_1$-$C_8$alkoxy; hydroxy$C_1$-$C_8$alkoxy; $C_1$-$C_8$alkoxy$C_1$-$C_8$alkoxy; aryl; aryl$C_1$-$C_8$alkoxy; heteroaryl; heteroaryl-$C_1$-$C_4$alkyl; 5 to 10 membered heterocyclic ring; nitro; carboxy; $C_2$-$C_8$alkoxycarbonyl; $C_2$-$C_8$alkylcarbonyl; —$N(C_1$-$C_8$alkyl)$C(O)$ $C_1$-$C_8$alkyl; —$N(R^{10})R^{11}$; —$CON(R^{10})R^{11}$; or —$C_1$-$C_4$-alkylene-$SO_2N(R^{10})R^{11}$; wherein each of $R^{10}$ and $R^{11}$ independently is hydrogen; hydroxy; $C_1$-$C_8$alkyl; $C_2$-$C_8$alkenyl; $C_3$-$C_8$cycloalkyl; $C_3$-$C_8$cycloalkyl-$C_1$-$C_8$alkyl; $C_1$-$C_8$alkoxy$C_1$-$C_8$alkyl; hydroxy$C_1$-$C_8$alkoxy$C_1$-$C_8$alkyl; hydroxy$C_1$-$C_8$alkyl; ($C_1$-$C_8$alkyl)-carbonyl; aryl$C_1$-$C_8$alkyl which optionally may be substituted on the ring by hydroxy, $C_1$-$C_8$alkoxy, carboxy or $C_2$-$C_8$alkoxycarbonyl; or 5 to 10 membered heterocyclic ring;
$R^4$ is hydrogen;
$R^5$ is hydrogen; halogen; $C_{1-4}$alkyl; or CF3;
$R^6$ is hydrogen;
each of $R^7$, $R^8$ and $R^9$ is independently hydrogen; hydroxy; $C_1$-$C_8$alkyl; $C_2$-$C_8$alkenyl; halo-$C_1$-$C_8$alkyl; $C_1$-$C_8$alkoxy; $C_3$-$C_8$cycloalkyl; $C_3$-$C_8$cycloalkyl$C_1$-$C_8$alkyl; aryl$C_1$-$C_8$alkyl; —Y—$R^{12}$ wherein Y is a direct bond or O and $R^{12}$ is a substituted or unsubstituted 5, 6 or 7 membered heterocyclic ring comprising 1, 2 or 3 heteroatoms selected from N, O and S; carboxy; ($C_1$-$C_8$alkoxy)-carbonyl; —$N(C_{1-8}$alkyl)—CO—$NR^{10}R^{11}$; —$CONR^{10}R^{11}$; —$N(R^{10})(R^{11})$; —$SO_2N(R^{10})R^{11}$; $R^7$ and R⁸ or R⁸ and R⁹, respectively form together with the carbon atoms to which they are attached, a 5 or 6 membered heteroaryl comprising 1, 2 or 3 heteroatoms selected from N, O and S; or a 5 or 6 membered carbocyclic ring;

wherein any alkyl, alkoxy, alkenyl, cycloalkyl, heterocyclic ring, aryl or heteroaryl may be unsubstituted or substituted by one or more substituents selected from halogen; OH; $C_1$-$C_8$alkyl; $C_1$-$C_8$alkoxy; nitro; cyano; COOH; carbamoyl; $C(NH_2)$=NOH; —$N(R^{10})R^{11}$; $C_3$-$C_6$cycloalkyl; 3 to 7 membered heterocyclic ring; phenyl; phenyl-$C_{1-4}$alkyl; 5 or 6 membered heteroaryl; in free form or salt form.

2. A compound according to claim 1 wherein at most one of $R^1$ or $R^3$ is —$CON(R^{10})R^{11}$.

3. A compound according to claim 1 which is a compound of formula $X_4$

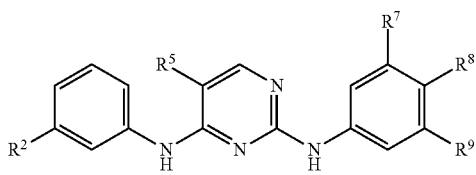

wherein $R^2$, $R^5$, $R^7$, $R^8$ and $R^9$ are as defined in claim 1.

4. A process for the production of a compound of formula I according to claim 1, comprising the steps of reacting a compound of formula II

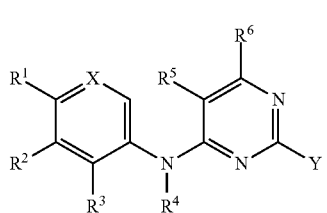

(II)

wherein $R^1$, $R^2$, $R^3$, $R^4$, $R^5$, $R^6$ and X are as defined in claim 1, and Y is a leaving group;
with a compound of formula III

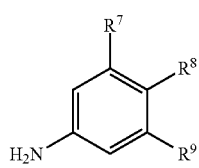

(III)

wherein $R^7$, $R^8$ and $R^9$ are as defined in claim 1;
and recovering the resulting compound of formula I in free form or in salt form, and, where required, converting the compound of formula I obtained in free form into the desired salt form, or vice versa.

5. A pharmaceutical composition comprising a compound of formula I according to claim 1 or a pharmaceutically acceptable salt thereof, together with one or more pharmaceutically acceptable carriers or diluents therefor.

6. A method for the treatment of breast cancer comprising administering to a subject in need thereof a therapeutically effective amount of a compound of formula I according to claim 1 in free form or in pharmaceutically acceptable salt form.

7. A combination which comprises (a) a therapeutically effective amount of a compound of formula I according to claim 1 for treatment of breast cancer and (b) one or more drug substances selected from the group consisting of:
cyclosporins; rapamycins; ascomycins; CCI-779; ABT578; AP23573; corticosteroids; prednisone; cyclophosphamide; azathioprine; methotrexate; gold salts; sulfasalazine; antimalarials; leflunomide; mizoribine; mycophenolic acid; mycophenolate mofetil; 15-deoxyspergualine; EDG receptor agonists having accelerating lymphocyte homing activity; immuno-suppressive monoclonal antibodies or their ligands; immunomodulatory compounds; anti proliferative agents; aromatase inhibitors; antiestrogens; topoisomerase I inhibitors; topoisomerase II inhibitors; microtubule active agents; alkylating agents; histone deacetylase inhibitors; famesyl transferase inhibitors; COX-2 inhibitors; MMP inhibitors; mTOR inhibitors; antineoplastic antimetabolites; platin compounds; compounds decreasing the protein kinase activity and anti-angiogenic compounds; gonadorelin agonists; anti-androgens; bengamides; bisphosphonates; anti proliferative antibodies; temozolomide; or an analog or derivative thereof.

8. A combination which comprises (a) a therapeutically effective amount of a compound of formula I according to claim 2 for treatment of breast cancer and (b) one or more drug substances selected from the group consisting of:
cyclosporins; rapamycins; ascomycins; CCI-779; ABT578; AP23573; corticosteroids; prednisone; cyclophosphamide; azathioprine; methotrexate; gold salts; sulfasalazine; antimalarials; leflunomide; mizoribine; mycophenolic acid; mycophenolate mofetil; 15-deoxyspergualine; EDG receptor agonists having accelerating lymphocyte homing activity; immuno-suppressive monoclonal antibodies or their ligands; immunomodulatory compounds; anti proliferative agents; aromatase inhibitors; antiestrogens; topoisomerase I inhibitors; topoisomerase II inhibitors; microtubule active agents; alkylating agents; histone deacetylase inhibitors; famesyl transferase inhibitors; COX-2 inhibitors; MMP inhibitors; mTOR inhibitors; antineoplastic antimetabolites; platin compounds; compounds decreasing the protein kinase activity and anti-angiogenic compounds; gonadorelin agonists; anti-androgens; bengamides; bisphosphonates; anti proliferative antibodies; temozolomide; or an analog or derivative thereof.

9. A combination which comprises (a) a therapeutically effective amount of a compound of formula I according to claim 3 for treatment of breast cancer and (b) one or more drug substances selected from the group consisting of:
cyclosporins; rapamycins; ascomycins; CCI-779; ABT578; AP23573; corticosteroids; prednisone; cyclophosphamide; azathioprine; methotrexate; gold salts; sulfasalazine; antimalarials; leflunomide; mizoribine; mycophenolic acid; mycophenolate mofetil; 15-deoxyspergualine; EDG receptor agonists having accelerating lymphocyte homing activity; immuno-suppressive monoclonal antibodies or their ligands; immunomodulatory compounds; anti proliferative agents; aromatase inhibitors; antiestrogens; topoisomerase I inhibitors; topoisomerase II inhibitors; microtubule active agents; alkylating agents; histone deacetylase inhibitors; famesyl transferase inhibitors; COX-2 inhibitors; MMP inhibitors; mTOR inhibitors; antineoplastic antimetabolites; platin compounds; compounds decreasing the protein kinase activity and anti-angiogenic compounds; gonadorelin agonists; anti-androgens; bengamides; bisphosphonates; anti proliferative antibodies; temozolomide; or an analog or derivative thereof.
10. A compound according to Formula I of claim 1, wherein the compound is
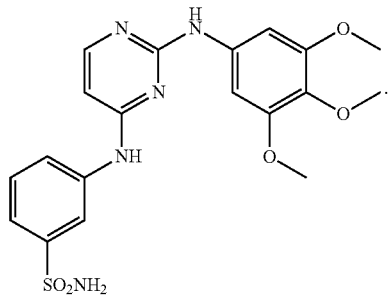 [SMILES: COc1cc(Nc2nccc(Nc3cccc(S(N)(=O)=O)c3)n2)cc(OC)c1OC]
* * * * *

SEQUENCE LISTING

```
<160> NUMBER OF SEQ ID NOS: 4

<210> SEQ ID NO 1
<211> LENGTH: 14
<212> TYPE: PRT
<213> ORGANISM: Artificial sequence
<220> FEATURE:
<223> OTHER INFORMATION: LAT-11 is a synthetic peptid substrate to be
      used in ZAP-70 kinase assay
<220> FEATURE:
<221> NAME/KEY: MISC_FEATURE
<222> LOCATION: (1)..(1)
<223> OTHER INFORMATION: E linked to L(+)-biotinyl-aminohexanoyl

<400> SEQUENCE: 1
```

```
Glu Glu Gly Ala Pro Asp Tyr Glu Asn Leu Gln Gln Leu Asn
1               5                   10

<210> SEQ ID NO 2
<211> LENGTH: 11
<212> TYPE: PRT
<213> ORGANISM: Artificial sequence
<220> FEATURE:
<223> OTHER INFORMATION: Biot-Y397 is a synthetic peptid substrate of
      human FAK protein tyrosine kinase (amino acid sequence 392 to 402
      of human biotin)
<220> FEATURE:
<221> NAME/KEY: MISC_FEATURE
<222> LOCATION: (1)..(1)
<223> OTHER INFORMATION: S linked to biotin

<400> SEQUENCE: 2

Ser Glu Thr Asp Asp Tyr Ala Glu Ile Ile Asp
1               5                   10

<210> SEQ ID NO 3
<211> LENGTH: 21
<212> TYPE: DNA
<213> ORGANISM: Artificial sequence
<220> FEATURE:
<223> OTHER INFORMATION: PCR primer for preparing human FAK cDNA

<400> SEQUENCE: 3
atggcagctg cttaccttga c                                              21

<210> SEQ ID NO 4
<211> LENGTH: 21
<212> TYPE: DNA
<213> ORGANISM: Artificial sequence
<220> FEATURE:
<223> OTHER INFORMATION: PCR primer for preparing human FAK cDNA

<400> SEQUENCE: 4
tcagtgtggt ctcgtctgcc c                                              21
```